US012118507B2

(12) United States Patent
Chila et al.

(10) Patent No.: US 12,118,507 B2
(45) Date of Patent: Oct. 15, 2024

(54) INVENTORY SYSTEM AND METHODS OF USING THE SAME

(71) Applicant: Ethicon, Inc., Somerville, NJ (US)

(72) Inventors: Matthew Chila, Somerville, NJ (US); Kevin McHale, Knoxville, TN (US); Alexander Weber, Knoxville, TN (US)

(73) Assignee: ETHICON, INC., Raritan, NJ (US)

( * ) Notice: Subject to any disclaimer, the term of this patent is extended or adjusted under 35 U.S.C. 154(b) by 279 days.

(21) Appl. No.: 17/490,495

(22) Filed: Sep. 30, 2021

(65) Prior Publication Data

US 2022/0104636 A1 Apr. 7, 2022

Related U.S. Application Data

(60) Provisional application No. 63/086,868, filed on Oct. 2, 2020.

(51) Int. Cl.
*G06Q 10/087* (2023.01)
*A47F 10/02* (2006.01)
(Continued)

(52) U.S. Cl.
CPC ....... *G06Q 10/087* (2013.01); *G01G 19/4144* (2013.01); *G01G 19/52* (2013.01);
(Continued)

(58) Field of Classification Search
CPC ............... G06Q 10/087; G06Q 10/109; G01G 19/4144; G01G 19/52; G16H 40/20;
(Continued)

(56) References Cited

U.S. PATENT DOCUMENTS 10,198,710 B1 * 2/2019 Hahn ................. G01G 19/4144
10,339,493 B1 7/2019 Famularo et al.
(Continued)

FOREIGN PATENT DOCUMENTS

KR 10-1890142 B1 8/2018

OTHER PUBLICATIONS

Carlson, Charles. Development of a Bed-based Nighttime Monitoring Toolset. Kansas State University ProQuest Dissertations Publishing, 2019. (Year: 2019).*

(Continued)

*Primary Examiner* — Florian M Zeender
*Assistant Examiner* — Fawaad Haider

(57) ABSTRACT

Systems, computer-readable instructions, and methods for storing products are disclosed. For example, the system may include modular shelving units that include a shelf which is placeable on a rack, the shelf including a platform, the shelf having a weight sensor below the platform, the platform is configured to support N number of holders, each of the N holders configured to store products, each shelf further having N−1 optical sensors below the N−1 holders when the N−1 holders are supported by the platform and N−1 windows above the N−1 optical sensors, the N−1 optical sensors being in proximity of the N−1 holders, respectively, wherein each holder includes an opening, wherein when a holder is on the shelf, the opening is capable of being aligned with an optical sensor, the shelf further having a processing circuit coupled to the N−1 optical sensors and the weight sensor.

20 Claims, 23 Drawing Sheets

(51) Int. Cl.
  *G01G 19/414* (2006.01)
  *G01G 19/52* (2006.01)
  *G16H 40/20* (2018.01)
  *G16H 40/40* (2018.01)
(52) U.S. Cl.
  CPC ............. *G16H 40/20* (2018.01); *G16H 40/40* (2018.01); *A47F 2010/025* (2013.01)
(58) Field of Classification Search
  CPC . G16H 40/40; A47F 2010/025; A47F 5/0025; A47F 10/02; A47B 47/0091; G01J 1/02
  USPC ......................................................... 705/28
  See application file for complete search history.

(56) References Cited

U.S. PATENT DOCUMENTS

2014/0297487 A1    10/2014  Bashkin
2019/0231467 A1*    8/2019  Grimsley ......... A61B 17/06133

OTHER PUBLICATIONS

Moreno, Asier et al. IVAN: Intelligent Van for the Distribution of Pharmaceutical Drugs. Sensors; Basel vol. 12, Iss. 5, (2012). (Year: 2012).*
International Search Report and Written Opinion dated Jan. 5, 2022 received in International Application No. PCT/IB2021/058991.

* cited by examiner

INVENTORY SYSTEM AND METHODS OF USING THE SAME

This application claims the benefit of and priority to U.S. Provisional Application Ser. No. 63/086,868 filed on Oct. 2, 2020, the entirety of which is incorporated by reference.

BACKGROUND OF THE DISCLOSURE

The present disclosure relates to storage and inventorying of various products, and more particularly to systems to store such products, and track and control an inventory of products in various locations, such as stores, warehouses, storage facilities, hospitals, clinics, out-patient surgical centers, or any other location that stores various products for use.

Medical products are one example of products that can be inventoried in the system and method of the present disclosure. In this example, in a typical hospital, many medical products are stored in a storage area, such as a closet or storage room. As one example, the storage and use of sutures is discussed. Typically, a hospital stores hundreds of different types of sutures on racks, in cabinets or in suture storage rooms. For a procedure, a medical worker may remove a number of sutures, and may possibly record the number and type of suture taken so the facility can maintain an accurate inventory of available sutures. However, actual inventory is typically a mere estimate at many facilities, due to the lack of accurate record keeping and due to the removal of medical products on an emergency basis.

In typical situations, little or no record keeping exists for any use of medical products and the urge to obtain more than what is reasonably expected for use is present, since further trips to a storage area are time and energy consuming. This creates further inefficiencies in a hospital's inventory management system and creates further instances of waste.

These typical systems lead to waste of sutures due to improper disposal or lack of restocking, and a higher incidence of product loss due to products passing their expiration dates. This typical system also does not track who is actually removing what type of suture or quantity of sutures from the storage closet, or if any unused sutures are actually ever restocked.

Further, storage of sutures within a typical hospital leads to waste. Because hospitals typically do not have a system to accurately and timely keep track of inventory, often either too many sutures are stored-leading to waste due to expiration of those sutures, or too few sutures are stored-leading to use of alternative sutures which may not be optimal for the specific procedure.

Also, management of inventory is a manual, time-consuming process, which typically includes a lag time of several days to account for shipping times, actual time for a person to manually restock, etc. Nurses and materials management staff usually split the responsibility of managing surgical product inventory. It is estimated that it takes hospital staff over 20 hours a week to manage suture products in the hospital. In 2016, the Association of Perioperative Registered Nurses reported that the national average base compensation was $70,300. Therefore, it is estimated that it costs hospital employers over $35,000 to have their operating room nurses manage their suture inventory.

Although the examples discussed above refer to sutures, any medical product can be included in as these typical examples.

In the field of surgery, for example, surgeons and other medical professionals rely on access to rooms of inventory having boxes of inventory manually stocked by themselves and sales representatives of the medical product manufacturers. These rooms require manual inventory control and simply hold the medical product. Also, these rooms may be a large distance from where a surgical procedure takes place, making the gathering of additional medical products not listed on a preference card difficult.

There is a need to develop an improved system for storing and maintaining the current inventory of medical products. Typically, different stock keeping units, or SKUs, need to be segregated by attributes such as diameter of suture, length of suture, color of suture, suture material (non-absorbable and absorbable), needle type, etc. As one example, one surgical suture manufacturer, Ethicon, Inc. of Somerville, NJ, has thousands of suture SKUs for various surgical procedures and other medical needs. This could translate to thousands of different suture boxes on the shelves in a larger hospital supply room. Product identification on each of the boxes is relatively small, and must be read carefully to select the appropriate medical product needed for a scheduled procedure or emergent/urgent situation. Given the manual nature of the current process, there are significant efforts in selection and restocking and inventory tracking. As indicated previously, it is estimated that a typical medium sized hospital may lose tens of thousands of dollars per year due directly to inefficiencies in the system.

As such, a need exists for better system for storing products, including sutures or other medical devices or supplies, and for otherwise more accurately and efficiently tracking inventory of such products.

Embodiments of the present disclosure provide devices and methods that address the above needs.

SUMMARY OF THE DISCLOSURE

The present disclosure is directed to systems and storage systems.

The present disclosure is also directed to modular shelving units that comprise: a shelf which is placeable on a rack, the shelf comprising a platform, the shelf having a weight sensor below the platform, the platform is configured to support N number of holders, each of the N holders configured to store products, each shelf further having N−1 optical sensors below the N−1 holders when the N−1 holders are supported by the platform and N−1 windows above the N−1 optical sensors, the N−1 optical sensors being in proximity of the N−1 holders, respectively, wherein each holder comprising an opening, wherein when a holder is on the shelf, the opening is capable of being aligned with an optical sensor, the shelf further having a processing circuit coupled to the N−1 optical sensors and the weight sensor, the processing circuit configured to: receive output from the weight sensor and one or more of the N−1 optical sensors or the weight sensor without the output from the one or more of the N−1 optical sensors; convert the respective outputs into a digital signal that comprises: (a) an identifier of the weight sensor and an identifier of one or more optical sensors when an output is received by the processing circuit from the one or more optical sensors; or (b) when no output is received from the one or more optical sensors, an identifier of the weight sensor, and in each instance, further comprises an indication of a weight or weight change associated with the output from the weight sensor; and transmit the digital signal to a terminal.

BRIEF DESCRIPTION OF THE DRAWINGS

The present disclosure will be better understood by reference to the following drawings, which are provided as illustrative of certain embodiments of the subject application, and not meant to limit the scope of the present disclosure.

FIG. 1 is a front view of a modular shelving system in accordance with aspects of the disclosure.

DETAILED DESCRIPTION

As used herein, the term "medical product" refers to products such as sutures, clips, staples, fasteners, implants, hemostats (absorbable), orthopaedic pins, screws, rods, plates, staple reloads, dressings, pacing wires, an endoscope, a clamp, a saw, bone wax, drains, connectors, adapters, tubing, topical skin adhesives, etc. that can be stored in a dispenser. The dispenser is further described below, but can refer to any device that is configured to store one or more medical products, dispense and/or allow access to that medical product, maintain and/or provide an inventory of stored products, and can accept unused medical products back into a storage compartment of the dispenser. Each medical product can include an identifier, the identifier can be any suitable identifying element, such as a bar code, a QR code, and/or a Radio Frequency Identification (RFID).

Figure 1:
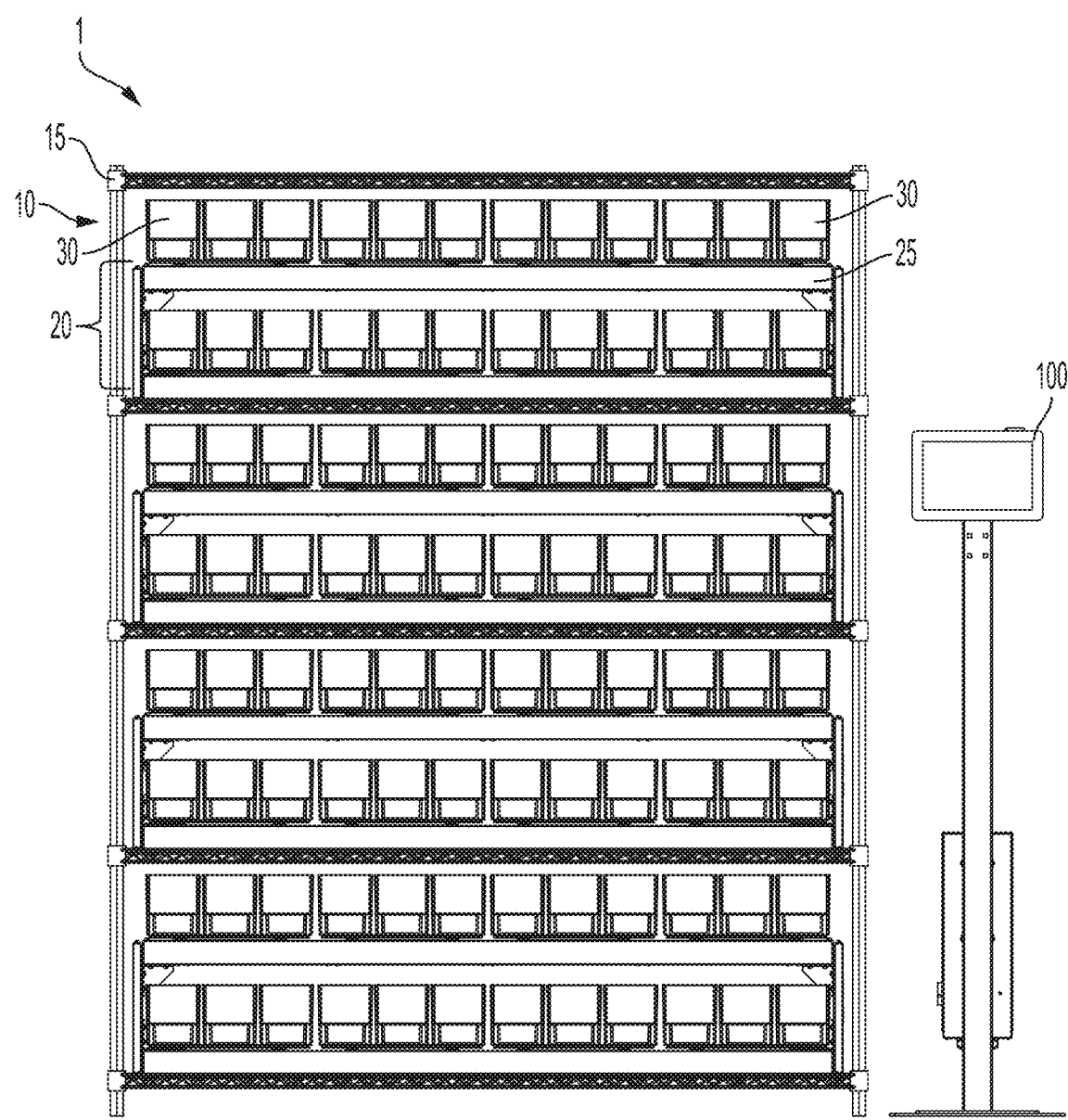

FIG. 1 is a front view of a modular shelving system 1 in accordance with aspects of the disclosure. The shelving system 1 comprises at least one shelving unit 10 and a terminal 100. Each shelving unit 10 comprises rack shelving 15. For example, the rack shelving 15 may be a standard 5-tier wire rack shelving. However, other rack shelving may be used. The rack is not limited to being made of wire. The rack shelving 15 may be a shelving unit existing in a hospital, such as in a supply room or an operating room. As depicted, the rack shelving 15 has four racks, however, the number of racks in the rack shelving 15 is not limited to four and may be based on the type of products, such as the types of medical products, stored in the shelving unit 10.

Figure 2:
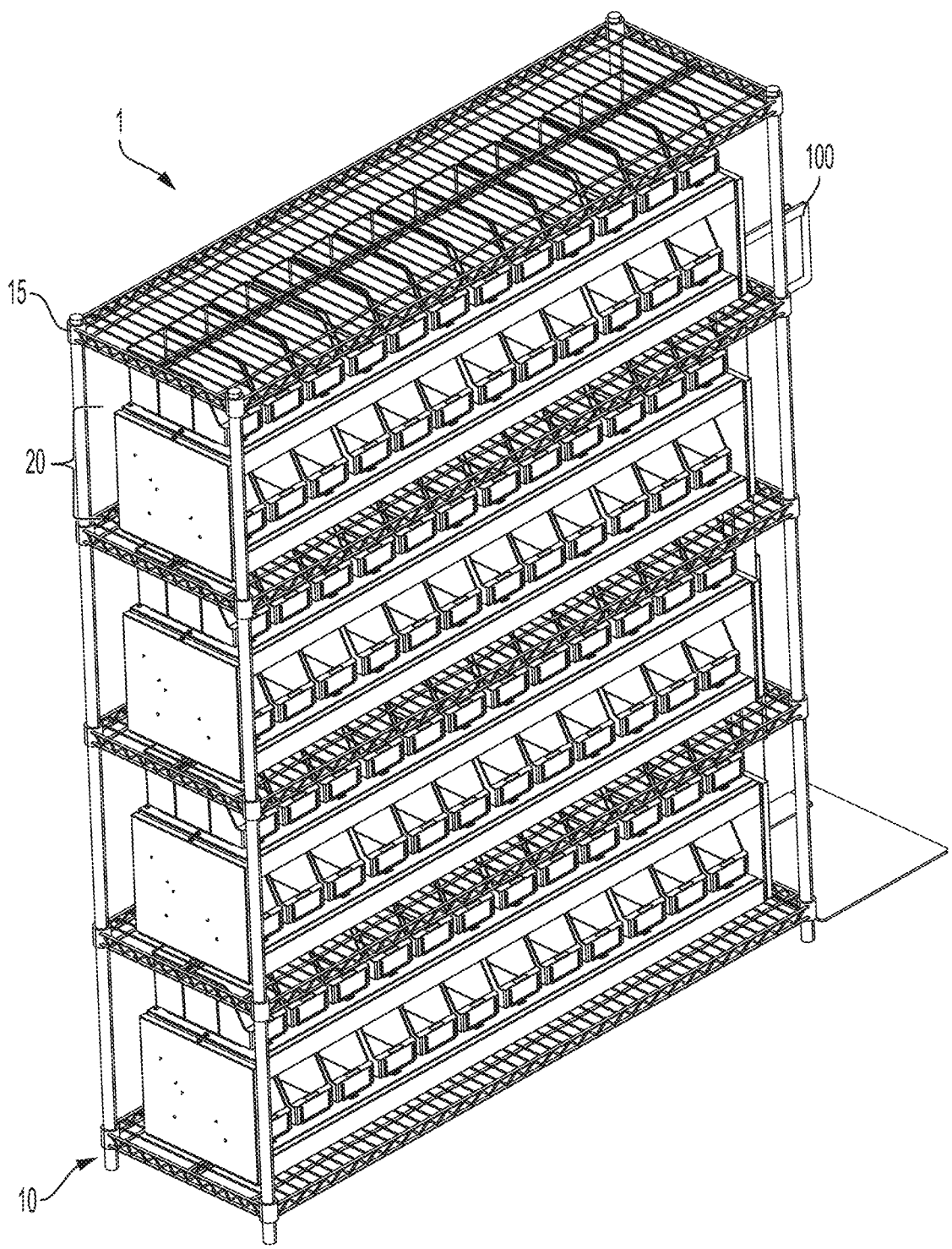
FIG. 2 is a perspective view of the modular shelving system in accordance with aspects of the disclosure.

Each shelving unit 10 contains one or more shelf assemblies 20. A shelf assembly 20 is supported by one of the racks. A shelf assembly 20 contains one or more shelves 25. As shown, the shelf assembly 20 has two shelves 25, however, the number of shelves is not limited to two and may be based on the number and type of products stored in the shelving unit 10. In an aspect of the disclosure, the distance between adjacent racks may be adjustable based on the number of shelves in the shelf assembly 20. As shown in FIGS. 1-2, the distance between adjacent racks allows for clearance for the two shelves 25 in the shelf assembly 20.

As depicted in FIGS. 1 and 2, there are four shelf assemblies 20, however, the number of shelf assemblies is not limited to four and may be based on the number and type of products stored in the shelving unit 10.

Additionally, as depicted in FIGS. 1 and 2, each shelf assembly 20 has the same number of shelves 25, however, different shelf assemblies 20 may have a different number of shelves 25.

Figure 3:
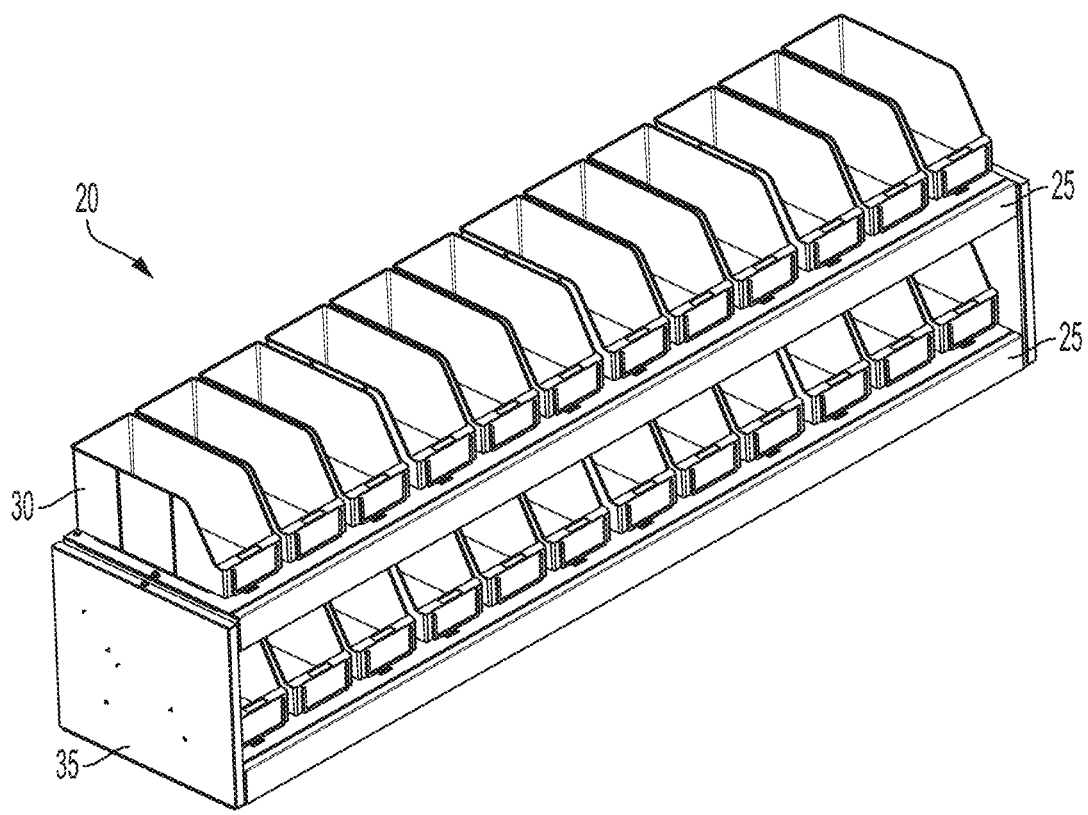
FIG. 3 is a perspective view of a shelving assembly in accordance with aspects of the disclosure.
Figure 4:
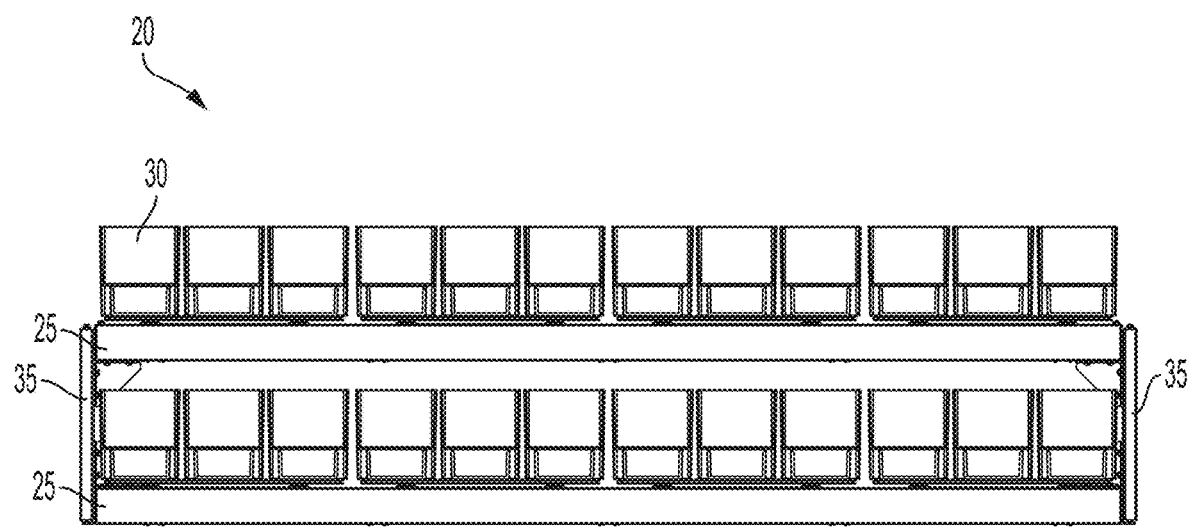
FIG. 4 is a front view of the shelving assembly.
Figure 5:
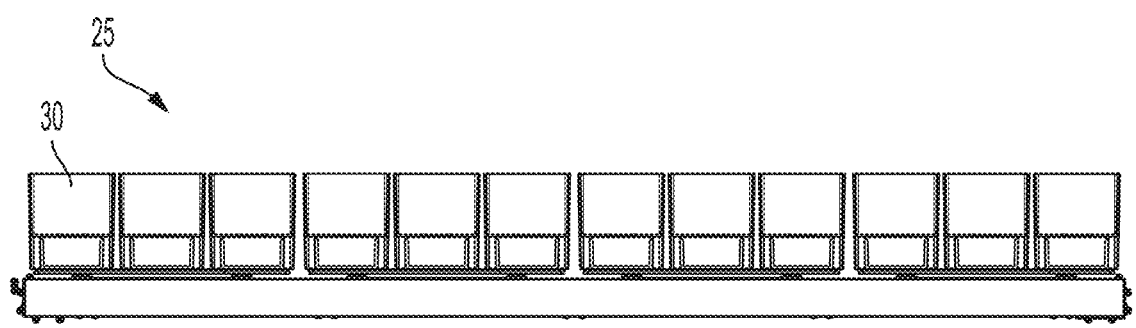
FIG. 5 is a front view of a shelf and bins in accordance with aspects of the disclosure.
Figure 6:
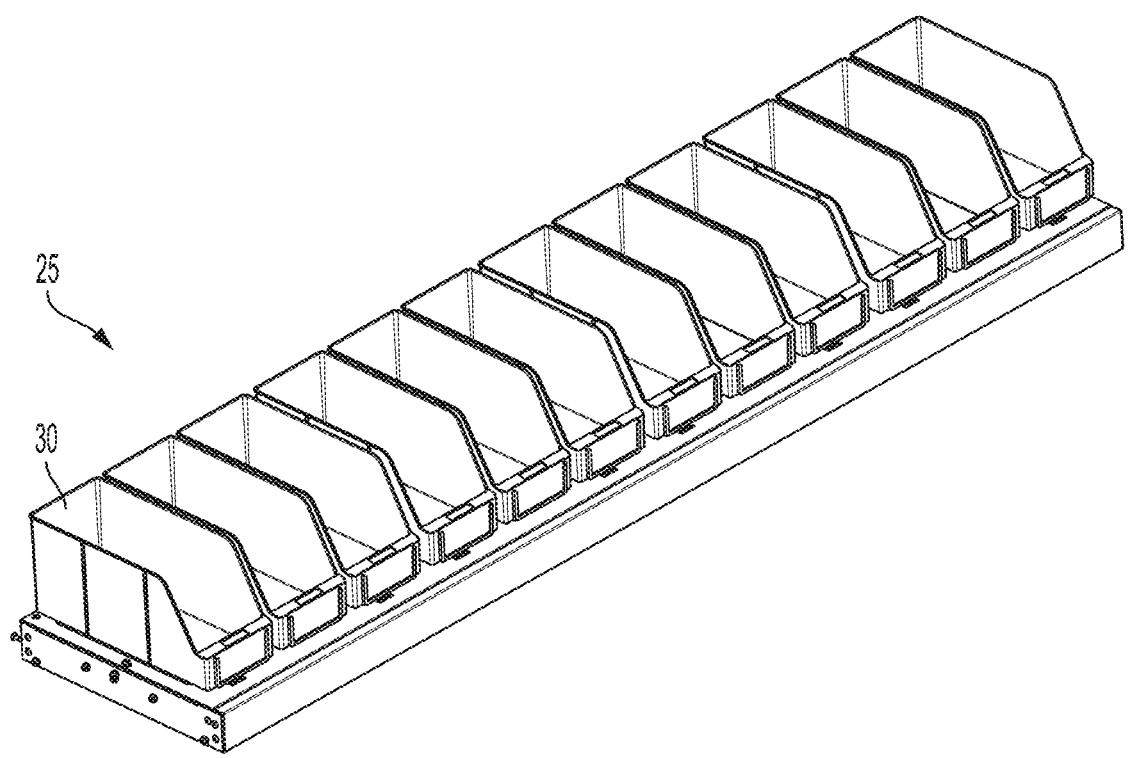
FIG. 6 is a perspective view of the shelf and bins in accordance with aspects of the disclosure.

An example of a shelf assembly 20 is depicted in FIGS. 3 and 4. The shelves 25 of the shelf assembly 20 are connected to each other by connecting walls 35. The shelves 25 may be connected to the walls 35 via mounting brackets. In an aspect of the disclosure, a communication bus 1600 (not shown in FIGS. 3 and 4) may be attached to the walls 35 to connect the communication bus 1600 to the shelves (processing circuits 1505 in each shelf 25). In other aspects of the disclosure, the connecting walls 35 may have internal channels for the communication bus 1600.

FIGS. 5-10 illustrate various views and/or portions of an example of a shelf 25 in accordance with aspects of the disclosure. Each shelf 25 is configured to support a plurality of bins 30. As depicted, the shelf 25 supports 12 bins. However, the number of bins is not limited to 12 and may be based on the number and type of products stored in the shelving unit 10. As depicted in FIGS. 1 and 2, each shelf 25 supports the same number of bins 30. However, each shelf 25 may support a different number of bins 30. For example, when the sizes of the products such as medical products are different, the number of bins 30 per shelf may be different.

Figure 8:
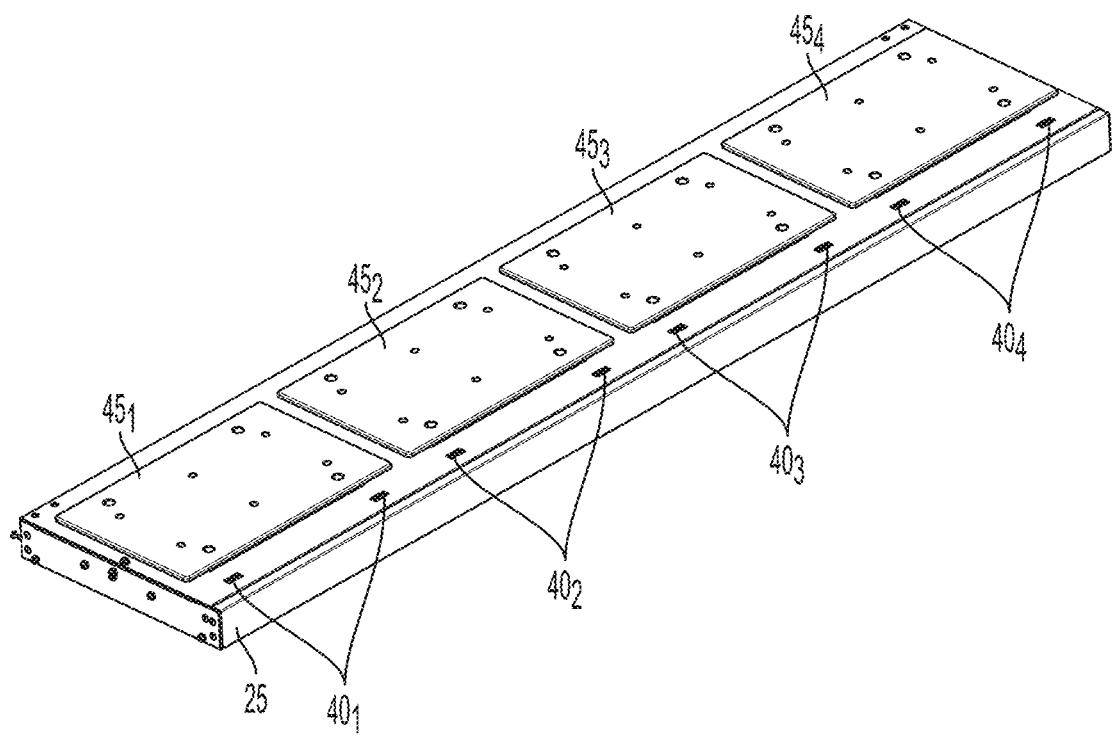
FIG. 8 is a perspective view of a shelf without the bins in accordance with aspects of the disclosure.
Figure 9:
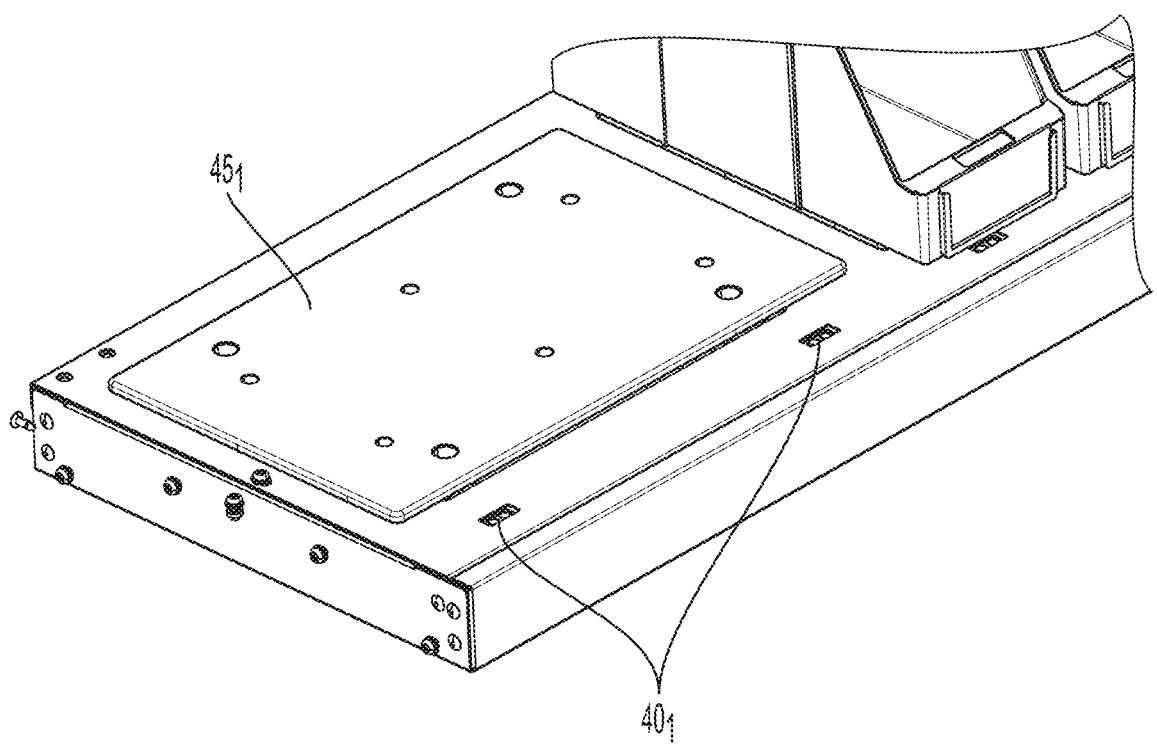
FIG. 9 is a perspective view of a portion of the shelf in accordance with aspects of the disclosure.
Figure 10:
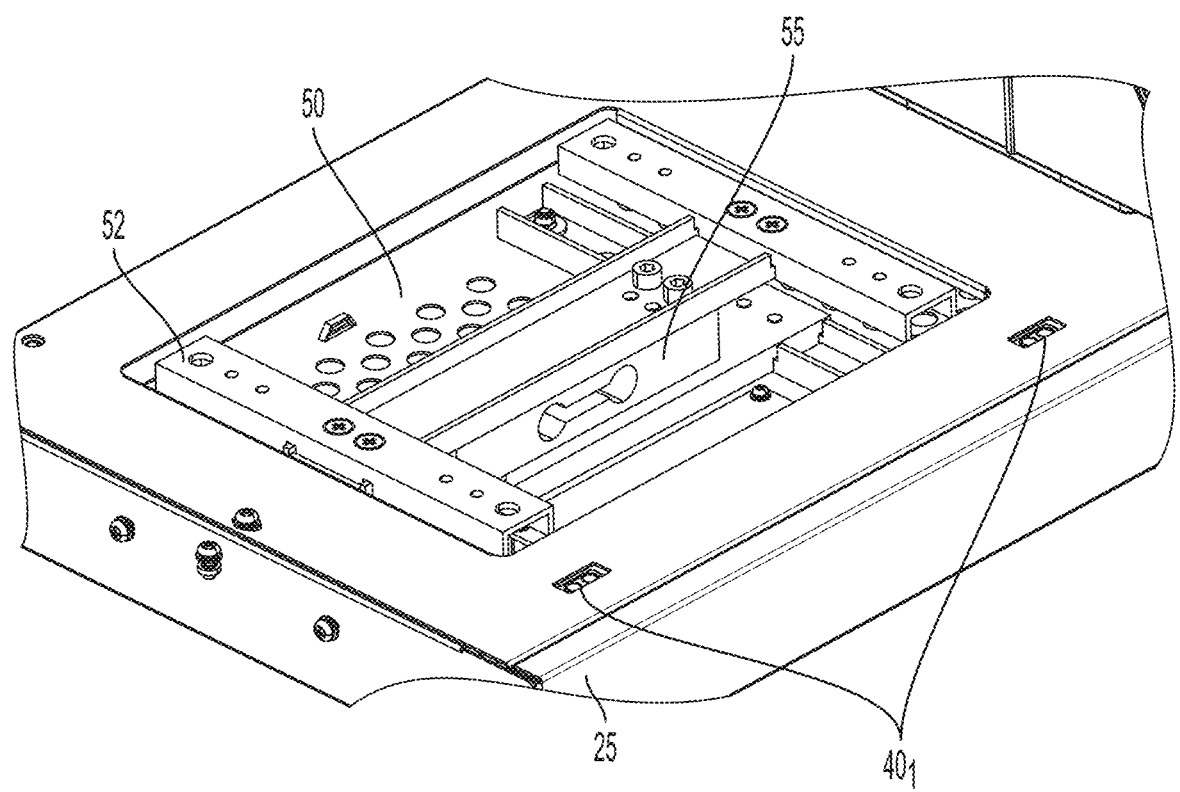
FIG. 10 is a perspective view of a portion of the shelf in accordance with aspects of the disclosure, with one of the platforms removed.

Each shelf 25 has a plurality of platforms $45_{1-N}$. FIG. 8 illustrates 4 such platforms $45_{1-4}$. Each platform 45 is capable of supporting a group of bins (N number of bins). The platform 45 may be moveable. As shown in FIG. 10, the shelves 25 have openings 50. A respective platform 45 covers a respective opening 50. In an aspect of the disclosure, a weight sensor 55 is located within each opening 50. The weight sensor 55 measures the weight of the bins 30 (with products) on the platform 45.

In an aspect of the disclosure, the weight sensor 55 may include a transducer such as a strain gauge. Other transducers may be used such as a capacitance transducer. However, in other aspects of the disclosure, different types of weight sensors may be used.

A platform 45 may be mounted to the shelf 25 on the support 52. The platform 45 may be secured to the shelf 25 via a friction fit. When one or more bins 30 with products, such as medical products, are placed on a platform 45, the platform and support 52 may move, which transfers the force caused by the bins/products to the weight sensor 55.

As depicted in the figures, each platform 45 supports three bins 30, however, the number of bins 30 is not limited to three. Also, the number of bins 30 per platform 45 may be different.

The shelf 25 further comprises a plurality of optical sensors 40. The optical sensors 40 are located in slots in the shelf 25. In an aspect of the disclosure, the optical sensors 40 are located near the front of the shelf 25. The optical sensors 40 are also located in front of a respective platform 45. In an aspect of the disclosure, the number of optical sensors 40 positioned in front of a respective platform 45 is one less than the number of bins 30 supported by the platform (N−1). For example, as depicted, there are two optical sensors 40 (also referred to an optical sensor group) per platform 45. However, the number of optical sensors 40 per platform 45 is not limited to two. In accordance with aspects of the disclosure, there is one bin 30 per platform 45 without an optical sensor 40. As shown in FIG. 8, the first platform $45_1$ has optical sensors $40_1$ and the second platform $45_2$ has optical sensors $40_2$, etc. . . . As depicted, the four platforms $45_{1-4}$ have four optical sensor groups. The position of the slots in the shelf 25 (and thus, the position of the optical sensors 40) may be based on the width and the length of the bins 30.

Figure 7:
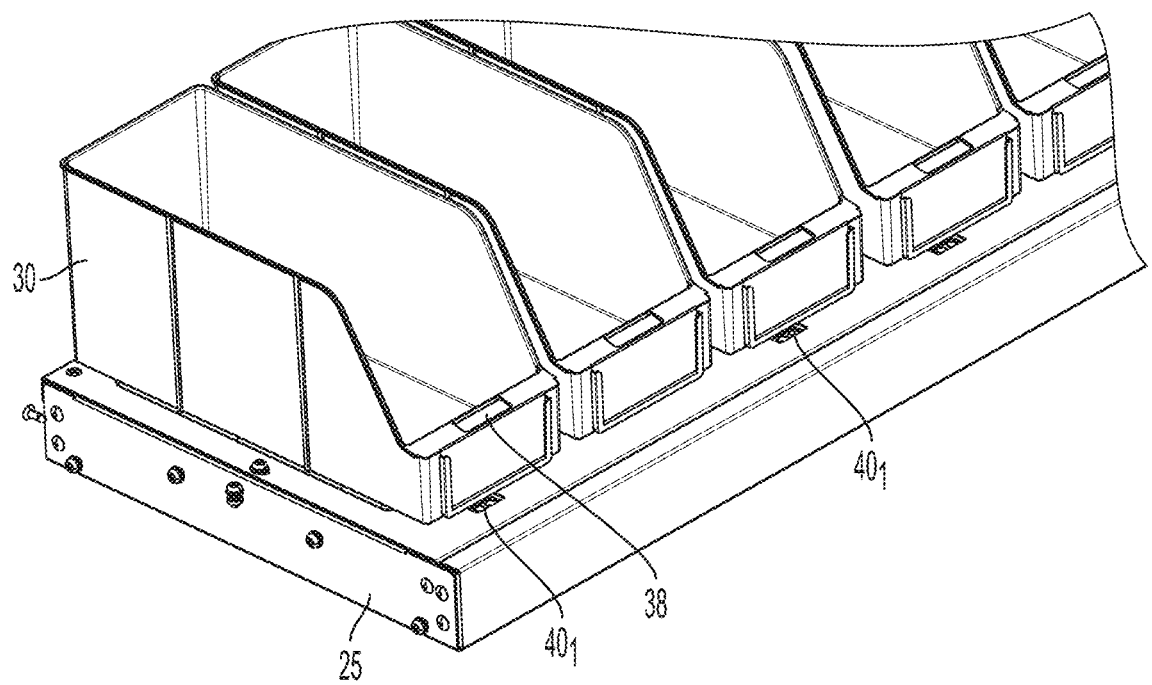
FIG. 7 is a view of a portion of the shelf with bins in accordance with aspects of the disclosure.

As depicted in FIGS. 7-8, the optical sensors 40 are positioned to align with the first and third bin (when three bins are placed on the platform).

In an aspect of the disclosure, the optical sensors 40 may be IR sensors. However, the optical sensor 40 is not limited to IR wavelength and may include visible or ultraviolet wavelengths. The optical sensor 40 may comprise an emitter-detector pair. Any suitable type of emitter may be used, but in some aspects, the emitter may be a light-emitting diode (LED). Any suitable detector capable of detecting light, such as a photodetector, may be used in the sensor. Examples of photodetectors include photodiodes, photoconductive cells, photoresistors, phototransistors, light to digital converters, and the like.

Figure 11:
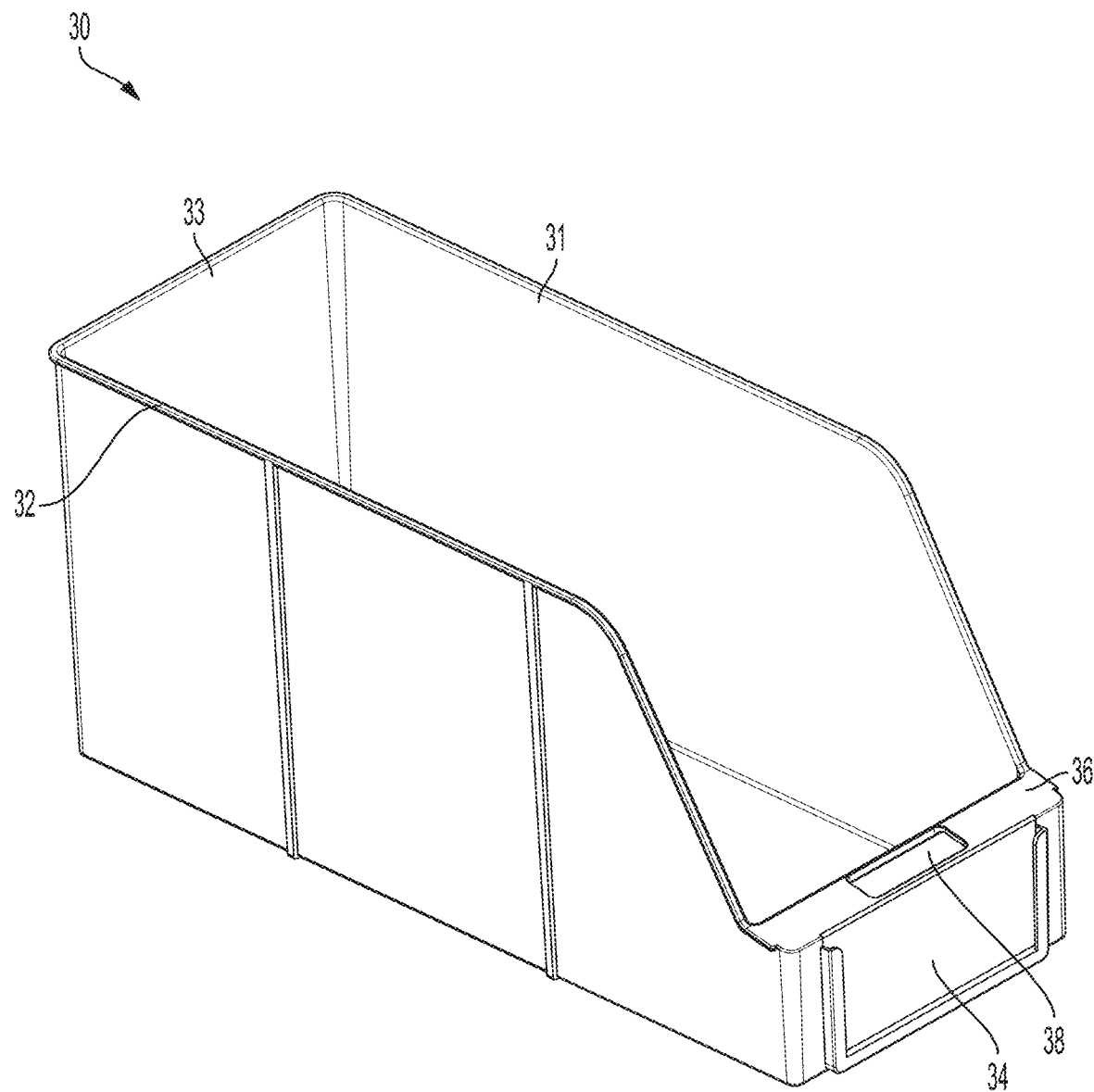
FIG. 11 is a perspective view of a bin in accordance with aspects of the disclosure.
Figure 12:
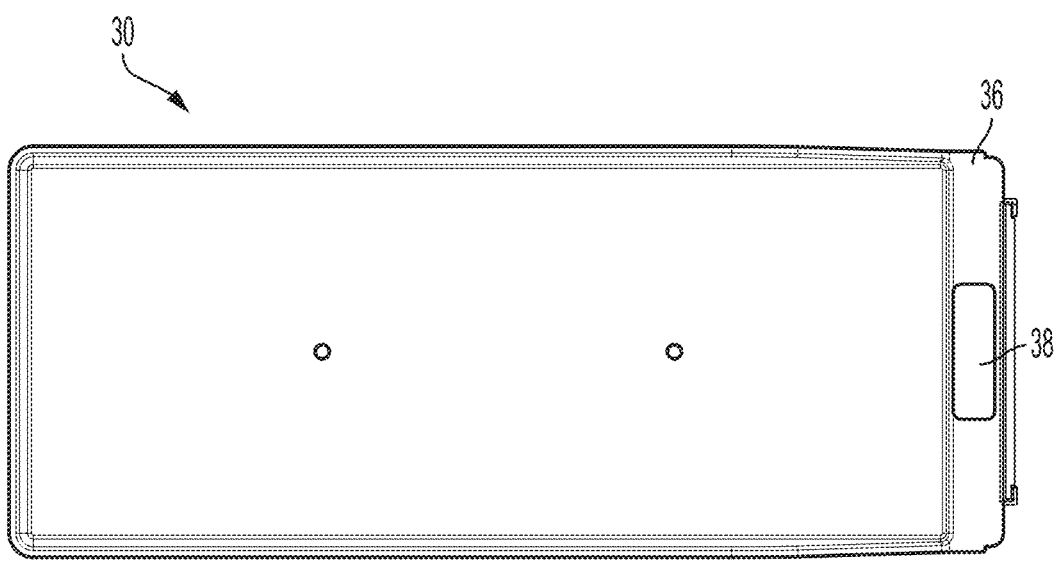
FIG. 12 is a top view of the bin in accordance with aspects of the disclosure.

An example of a bin 30 is shown in FIGS. 11 and 12. The bin 30 has sidewalls 31, 32, a rear wall 33 and a front wall 34. The walls 31, 32, 33, and 34 form a compartment for products, such as medical products, to be stored. The sidewalls 31, 32 prevent lateral movement of the products once the products are stored in the compartment. The bin further has a slot 38. The slot 38 (or opening), when the bin 30 is placed on a platform 45 may align with an optical sensor 40 (if the bin 30 is in a position where the optical sensor 40 is located (e.g., first bin or third bin). In an aspect of the disclosure, the slot 38 may be in a rearward projection 36 from the front wall 34. The rearward projection 36 may extend from the sidewalls 31, 32. In other aspects, the slot 38 may be in the frontwall 34.

A product, such as a medical product, may be manually removed from a bin 30 by a person, such as a nurse, moving his/her hand into the bin 30 from the front (to enter the compartment) and take the product.

Figure 13:
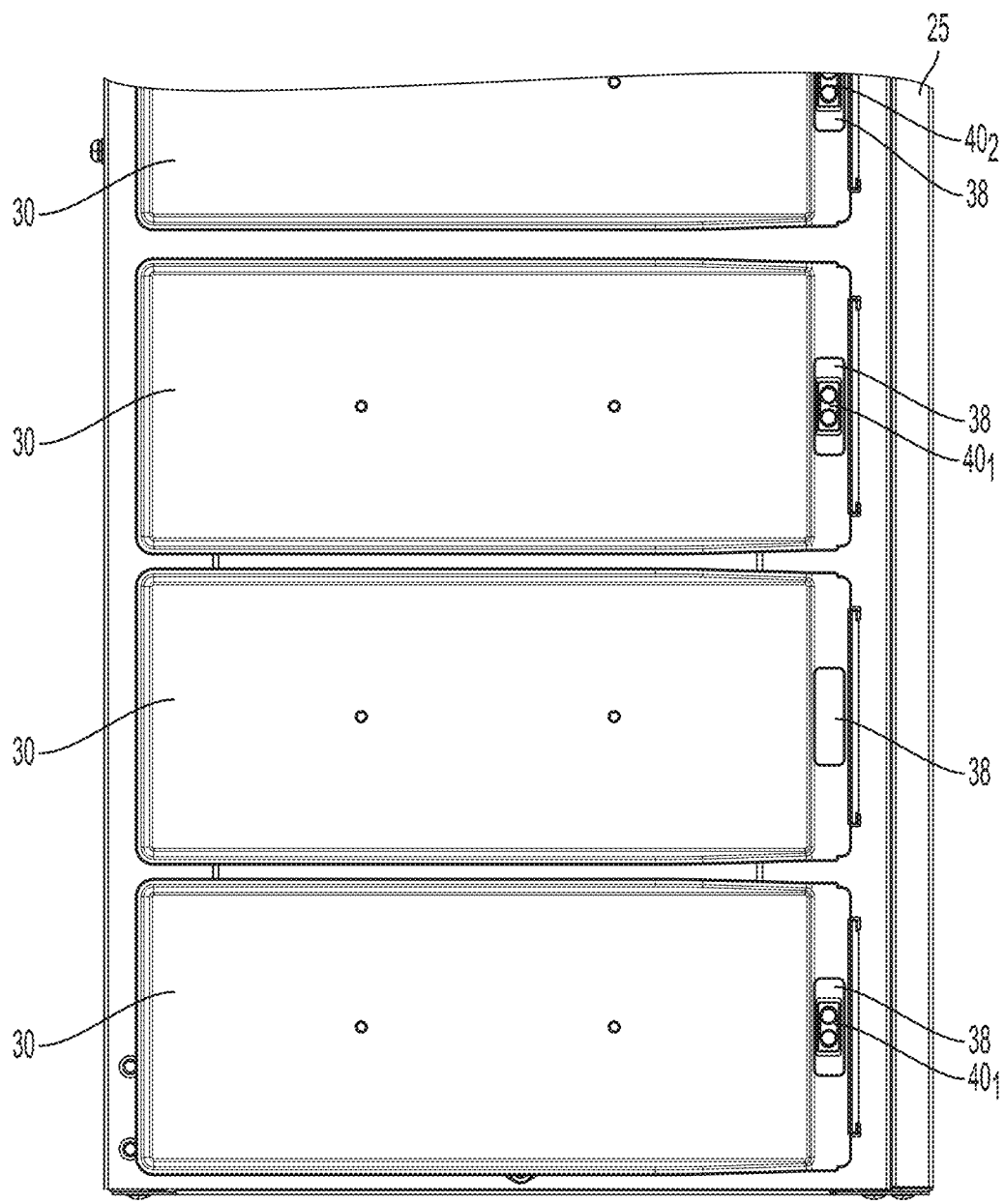
FIG. 13 is a top view of a portion of a shelf with bins in accordance with aspects of the disclosure.

FIG. 13 is a top view illustrating a portion of the shelf 25 and some bins 30. As can be seen, the slot 38 in the bin 30 aligns with the optical sensors 401 for two of the three full bins shown. The middle full bin 30 shown in FIG. 13 does not align since there is no optical sensor adjacent to the bin 30. The bin 30 partially shown may align with an optical sensor 40 from another group as the bin 30 is on another platform, e.g., $45_2$.

Figure 14:
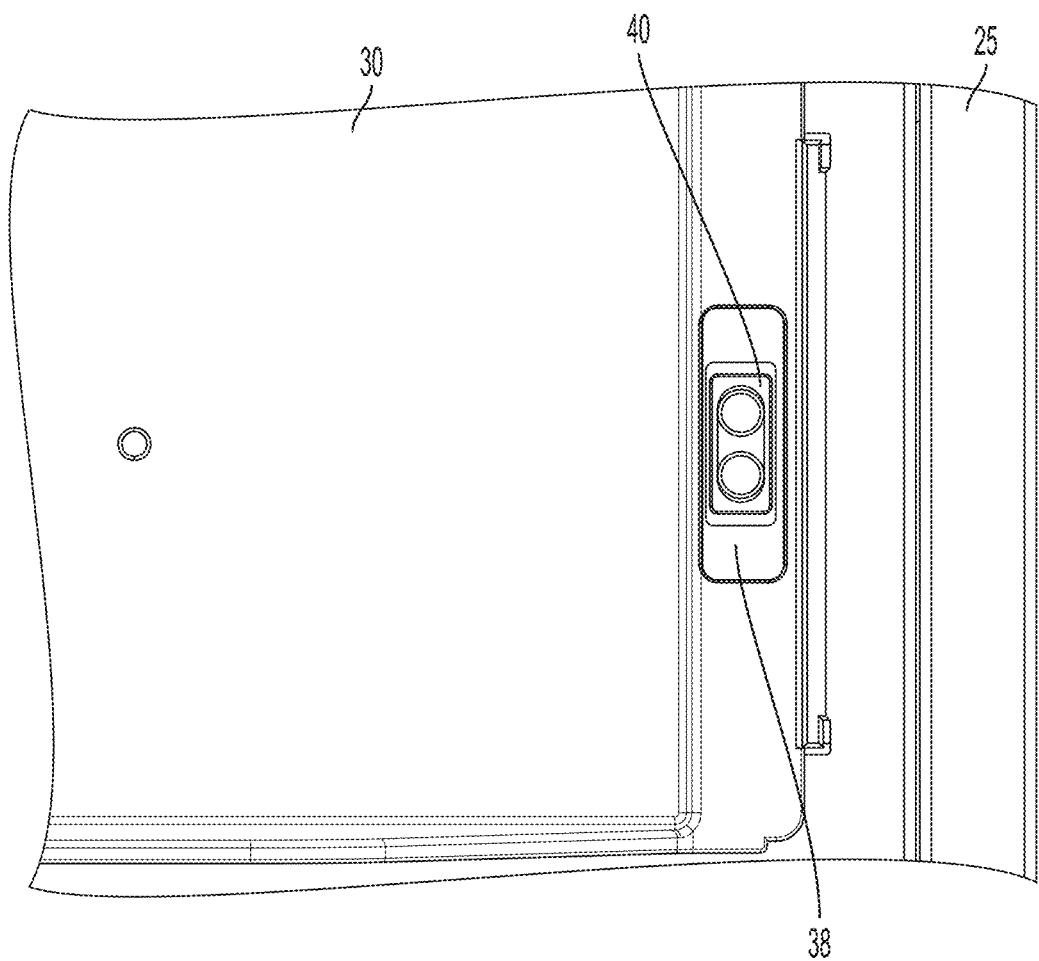
FIG. 14 is a top view of a portion of a shelf with a portion of the bin in accordance with aspects of the disclosure.

The alignment of the slot 38 and an optical sensor 40 is also shown in FIG. 14.

In an aspect of the disclosure, the optical sensors 40 may be covered by a transparent window (not shown) to prevent the optical sensors 40 from being touched. The transparent window may be transparent to the wavelength emitted by the optical sensor 40.

Inventory, e.g., products, may be tracked by using both the optical sensors 40 and weight sensors 55 to determine removal of the products from different inventory locations, e.g., bins 30. For example, the weight sensor 55 may be used to determine how may products are removed from a respective platform 45, e.g., any of the bins 30 on the platform 45, while the optical sensor 40 may be used to determine which location on the platform 45, the product was removed from, e.g., bin.

Figure 15:
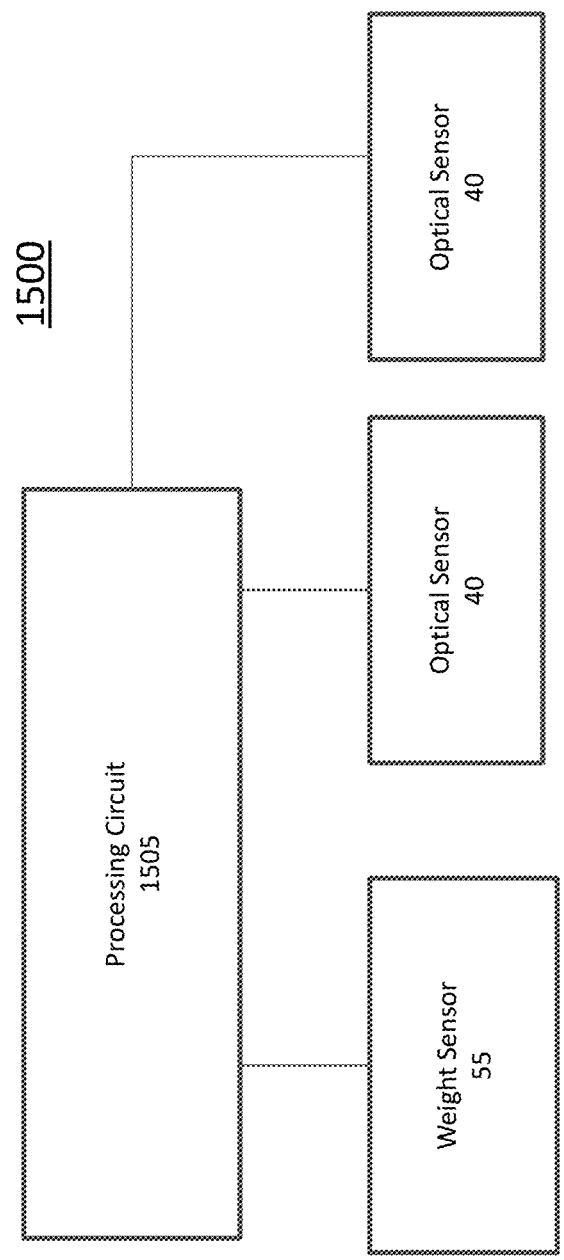
FIG. 15 illustrates a block diagram of a sensing unit for a platform in accordance with aspects of the disclosure.

FIG. 15 illustrates a block diagram of a sensing unit 1500 for a platform 45 in accordance with aspects of the disclosure. Each platform 45 has its own sensing unit 1500. The sensing unit 1500 comprises both types of sensors: the weight sensor 55 and the optical sensor 40. The sensing unit 1500 further comprises a processing circuit 1505.

As described above, the weight sensor 55 may include a transducer such as a strain gauge. The strain gauge has a resistance which various with a change in the length. The length may be changed when a force is applied to the strain gauge. The change may be measured from terminals in the weight sensor 55. There may be a voltage change due to the force which is measureable.

In an aspect of the disclosure, the voltage may be measured using a bridge circuit such as a wheatstone bridge as a readout circuit, e.g., an electric circuit that is capable of measuring the minute changes in resistance corresponding to strain. The variable resistance of the strain gauge may be one or more of the legs of the bridge where the other legs have a fixed resistance. The fixed resistance may be set to equal the resistance of the strain gauge with no force applied, e.g., no bins and products on the platform 45. A voltage is applied to two of the points of the bridge. The measured voltage output is determined at the other two points of the bridge. When no force is applied, the measured voltage output is zero. However, when the resistance of the strain gauge is changed due to force, the bridge will become unbalanced and a voltage will exist at the output terminals. This change in the measured voltage output may be converted into a strain or force measure based on Gauge factor GF. The gauge factor depends on the material used in the strain gauge and the type of gauge. In some aspects, the strain gauge may be all of the legs of the bridge.

The input voltage to the bridge may be supplied from a power source. The power source may be supplied via a power bus (not shown). The power bus may be included in the same cable as the communication bus. However, in other aspects, the power bus may be in a separate cable.

In an aspect of the disclosure, the bridge may be incorporated into the weight sensor 55. However, in other aspects of the disclosure, the bridge may be incorporated into the processing circuit 1505.

The electric circuit used to measure the change in resistance is not limited to a wheatstone bridge and other electric circuits may be used. For example, a multi-wire resistance circuit may be used such as a four-wire ohm circuit. A four-wire ohm circuit may comprise a voltmeter, a current source and resistance. For example, four resistors may be placed in series with the strain gauge. The resistance of the four resistors may be the same. The voltmeter measures the voltage drop across the strain gauge when a low current is supplied by the current source. The resistance is determined from the value of the low current and the voltage drop. In an aspect of the disclosure, the weight sensor 55 may further include a processing element to determine the resistance from the voltage and current values. In other aspects of the disclosure, the processing circuit 1505 may receive the measured voltage values and applied low current and determine the resistance.

The above measurement may be made twice to determine the strain or force on the strain gauge. For example, first a value of gauge resistance in an unstrained condition may be determined and then a value of the gauge resistance is determined with strain applied. A difference in the measured gauge resistances divided by the unstrained resistance gives a fractional value of the strain (this value and the GF can be used to determine force and weight).

In some aspects of the disclosure, the weight sensor 55 may include an electronic storage device. The electronic storage device may include a look up table. The look up table may include a correspondence between measure voltages and weights. In other aspects, the look up table may include a correspondence between the determined resistance and weights. In other aspects, the look up table may include a correspondence between a change in resistance and a change in weight. Thus, the look up table may be used to determine the weight. In other aspects, the weight may be directly calculated using one or more equations from the resistance. In this aspect, the electronic storage device may also include the last weight measurement determined by the weight sensor 55.

Further, in an aspect of the disclosure, the weight sensor 55 may include a processing element configured to determine whether a weight change is greater than a preset weight (threshold). For example, the preset weight may be 1 g. This preset weight is not limited to 1 g and may be based on the application and the intended products stored in the bin 30. The preset weight may be changed, as needed. For example, the processing element may include a differential or operational amplifier set with the preset weight. When the change is less than the preset weight, the weight sensor 55 may not transmit the weight or weight change to the processing circuit 1505. When the weight or change in weight is greater than the preset weight, the weight sensor 55 transmits the weight or weight change to the processing circuit 1505.

In other aspects of the disclosure, instead of a preset weight, the threshold may be used based on another measured value such as a change in resistance or measured voltage, e.g., without a conversion to a weight.

The weight sensor 55 is connected to the processing circuit 1505. In an aspect of the disclosure, the connection is a wired connection, e.g., direct connection. However, in other aspects of the disclosure, the weight sensor 55 may have a wireless interface.

In an aspect of the disclosure, a processing circuit 1505 comprises at least a processor and an electronic storage device. As used herein, the term "processor" may refer to, is part of, or includes circuitry capable of sequentially and automatically carrying out a sequence of arithmetic or logical operations; recording, storing, and/or transferring digital data. The term "processor" may refer to one or more application processors, one or more baseband processors, a physical central processing unit (CPU), a single or multiple-core processor, and/or any other device capable of executing or otherwise operating computer-executable instructions, such as program code, software modules, and/or functional processes. In other aspects, the processor may be integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

The processing circuit 1505 may also include an analog to digital converter (ADC). The ADC may convert the analog information received from the weight sensor 55 and the optical sensors 40 into a digital value for further processing by the processor. For example, when the weight sensor 55 output a voltage or resistance or weight (or change in weight), the ADC may convert the same into the digital value.

As described above, in an aspect of the disclosure, the processing circuit 1505 may include the electric circuit used to measure the change in resistance. Therefore, the processor in the processing circuit 1505 may determine the resistance based on the detected voltage (which is converted into digital via the ADC). Additionally, the processor may determine from the resistance or voltage a weight or a change in weight. In an aspect of the disclosure, the process may directly calculate the weight or change in weight using one or more equations.

In other aspects of the disclosure, the electronic storage device in the processing circuit 1505 may include a look up table. The look up table may include a correspondence between measure voltages and weights. In other aspects, the look up table may include a correspondence between the determined resistance and weights. In other aspects, the look up table may include a correspondence between a change in resistance and a change in weight. Thus, the look up table may be used to determine the weight.

The electronic storage device in the processing circuit 1505 may include the last weight measurement determined by the processing circuit 1505.

Further, in an aspect of the disclosure, the processing circuit 1505 may be configured to determine whether a weight change is greater than a preset weight using the last weight measurement (determination) in the electronic storage device. For example, the preset weight may be 1 g. This preset weight is not limited to 1 g and may be based on the application and the intended products stored in the bin. The preset weight may be changed, as needed. When the change is less than the preset weight, the processing circuit 1505 may not transmit the weight or weight change to the terminal 100. When the weight or change in weight is greater than the preset weight, the processing circuit 1505 transmits the weight or weight change to the terminal 100.

In other aspects of the disclosure, instead of a preset weight, the threshold may be used based on another measured value such as a change in resistance or measured voltage, e.g., without a conversion to a weight.

The processing circuit 1505 is also connected to one or more optical sensors 40. For purposes of the description, FIG. 15 shows two optical sensors 40 for the platform 45. The optical sensors may be directly connected to the processing circuit 1505. In other aspects, the optical sensors may have a wireless communication interface.

As described above, the optical sensor 40 may includes an emitter and a detector. When a person attempts to remove a product from the bin 30, the hand and/or product may be positioned over the slot 38. The emitter may transmit an IR signal. The IR signal may bounce off from a surface of any object and is received by the detector. When a hand and/or product is not over the slot 38, the IR signal may bounce of another shelf assembly 20 or shelf 25. However, when the hand and/or product is over the slot 38, the IR signal may bounce off the hand and/or product. Thus, there is a different amount of light that reaches the detector when the hand and/or product is over the slot 38 than when it is not. This difference causes in a change in the resistance of the detector, e.g., photodetector. The change in resistance results in a measureable change in a voltage. In an aspect of the disclosure, the detector, e.g., photodetector, may be connected to a terminal of an operational amplifier (Op-Amp). The other terminal of the operational amplifier may be set with a threshold. The threshold may be based on a calibration, e.g., amount of light when the no hand or product is located over the slot 38. The threshold may be different for different optical sensors 40 in the modular shelving unit 10 depending on the location. For example, when the optical sensor 40 is on the top shelf, the light received by the detector of the sensor 40 under a normal condition may be different than the light received by the detector of the sensor 40 under a normal condition where the optical sensor 40 located on the bottom shelf. When there is no hand or product over the slot, the Optical Sensor output OFF, e.g., no detection. However, when a hand or product is over the slot 38, the resistance changes, resulting in the OP-Amp outputting a high value, e.g., ON. The output is sent to the processing circuit 1505.

For example, the ON signal, is received by the processing circuit 1505 and converted by the ADC into a digital value for the processor. In an aspect of the disclosure, each optical sensor 40 is individually addressable and this address is included in the ON signal. In other aspects, the address is based on which connection received the ON signal.

The electronic storage device in the processing circuit 1505 can include computer system readable media in the form of volatile memory, such as random access memory (RAM) and/or cache memory or others. In some aspects, multiple electronic storage devices may be used. The electronic storage device may be any type of integrated circuit or other storage device adapted for storing data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

Figure 16:
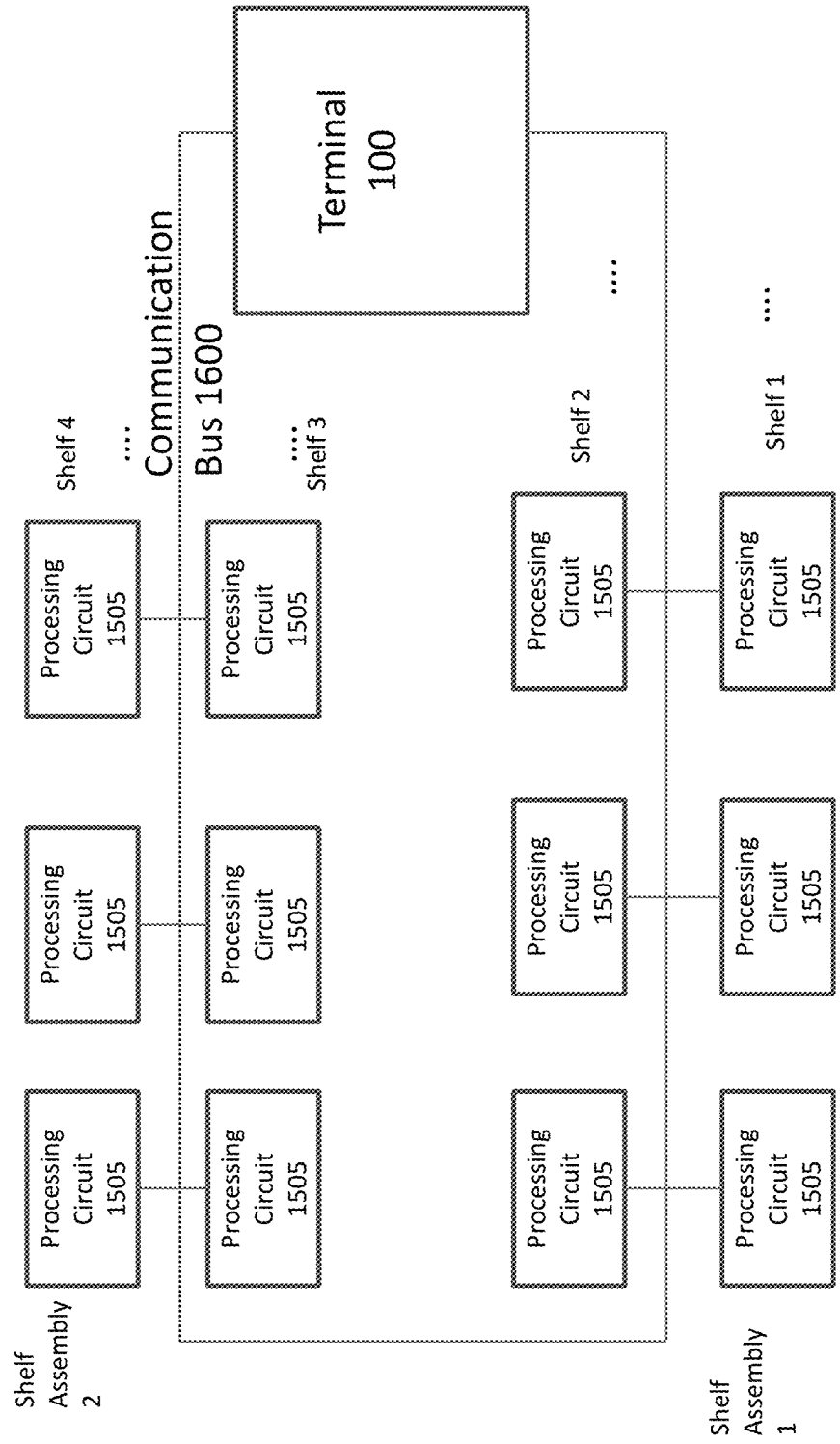
FIG. 16 illustrates a communication bus in accordance with aspects of the disclosure between the processing circuits and the terminal.

Each processing circuit 1505 may communicate with the terminal 100. FIG. 16 illustrates a diagram showing an example of the communication bus 1600. In an aspect of the disclosure, the communication bus 1600 is an RS485 bus. The RS485 bus may be used for serial communication. In an aspect of the disclosure, the same bus may be used to supply power to each processing circuit 1505 and the sensors (using a different wire). In other aspects, a different bus may be used. The terminal 100 is the master node and each processing circuit 1505 is the slave. Each processing circuit 1505 may have a driver or communication interface for the RS485 bus.

Figure 17:
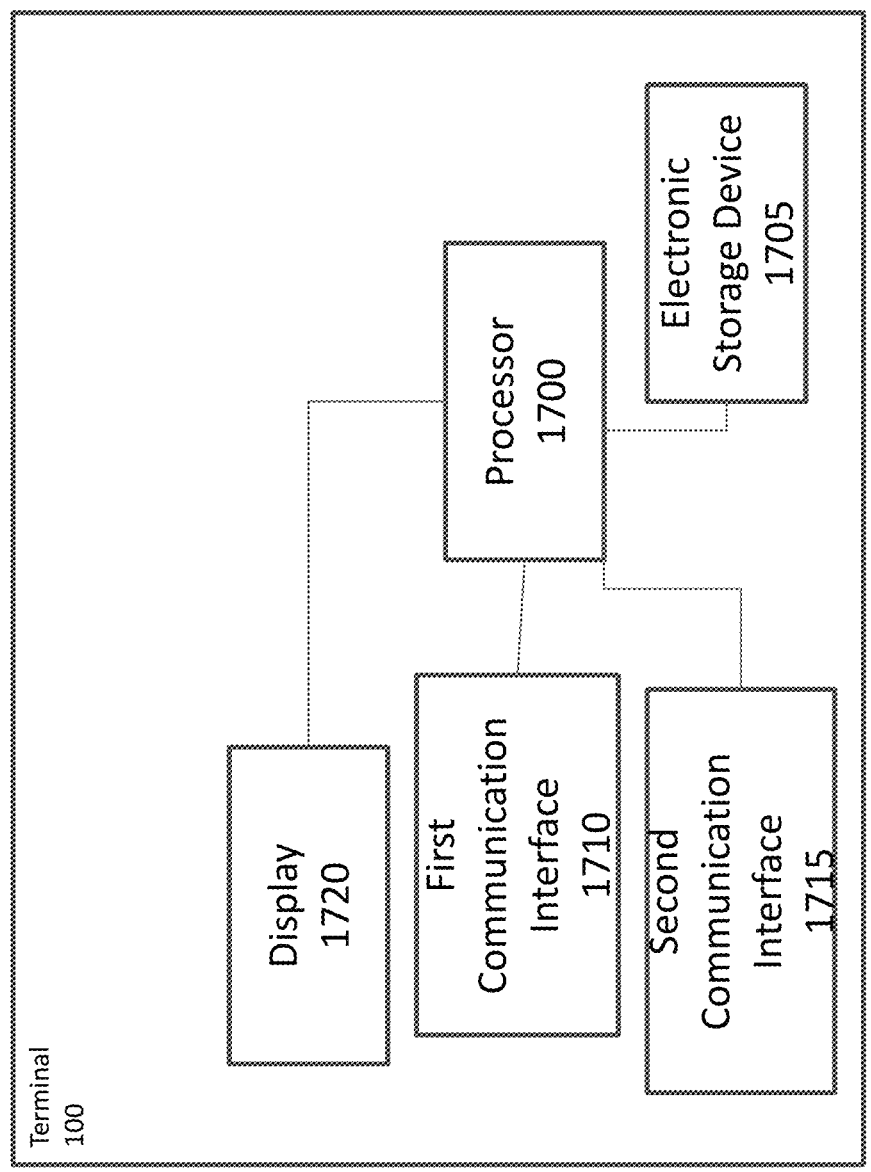
FIG. 17 illustrates a block diagram of a terminal in accordance with aspects of the disclosure.

FIG. 17 illustrates a block diagram of a terminal 100 in accordance with aspects of the disclosure.

The terminal 100 may be a mobile telephone, tablet, portable laptop, personnel computer, etc. The terminal 100 includes a processor 1700, an electronic storage device 1705, a first communication interface 1710, a second communication interface 1715 and a display 1720.

The first communication interface 1710 may be an RS485 communication interface and driver. The first communication interface 1710 may be used to communicate with the processing circuits 1505 for each platform 45, respectively. The second communication interface 1715 may be a wireless communication interface such as a WIFI interface. The second communication interface 1715 may be used to communicate with a server.

The display 1720 may have a touchscreen. The display 1720 is configured to display screens. The screens may include information regarding the products stored in the modular shelving unit 10. In other aspects of the disclosure, the screens may include information regarding a scheduled medical procedure such as a schedule code and/or an operating room number.

Figure 18:
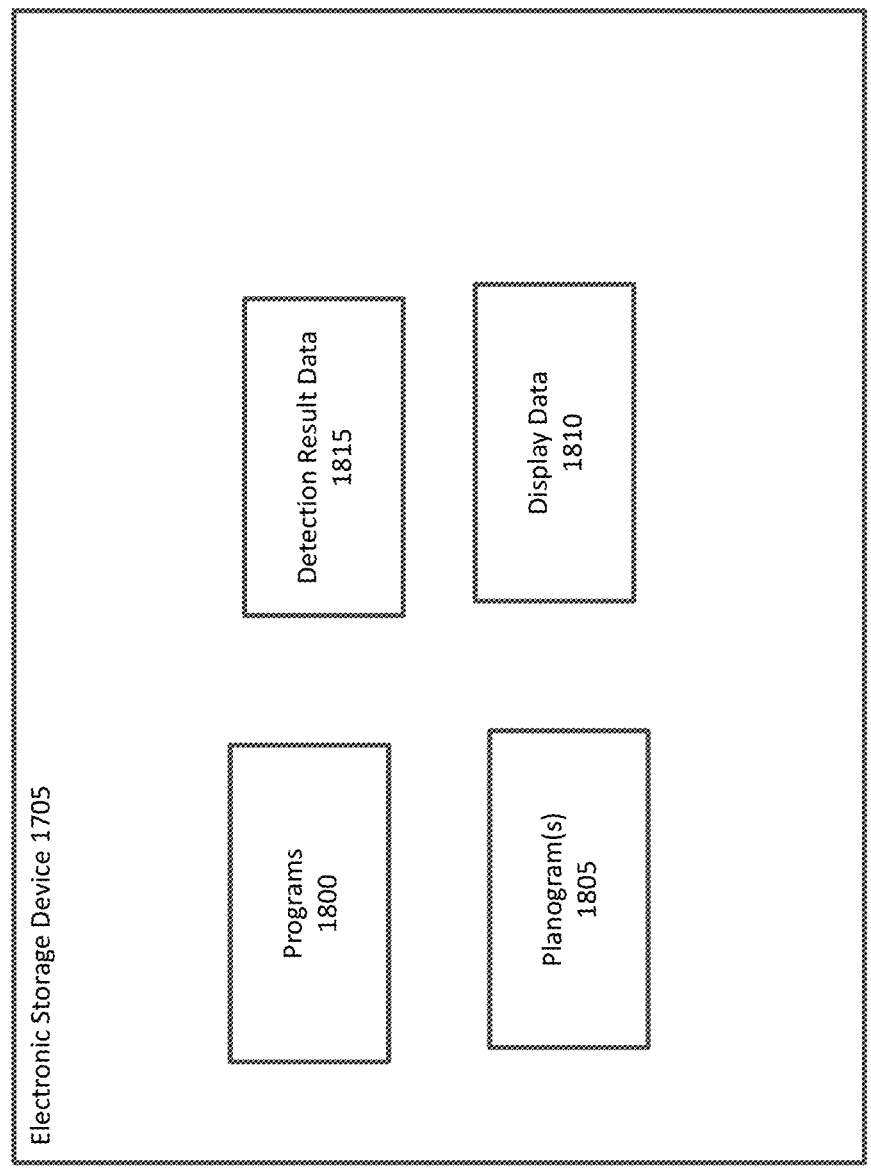
FIG. 18 illustrates a diagram of information stored in an electronic storage device of the terminal in accordance with aspects of the disclosure.

FIG. 18 illustrates a diagram of information stored in the electronic storage device 1705 in accordance with aspects of the disclosure. The electronic storage device 1705 may store program(s) or modules 1800, planogram(s) 1805, display data 1810 and detection result data 1815.

The program(s) or module(s) 1800 enable performance of the methods and functions described herein. The programs(s) or module(s) 1800 may be programmed into the integrated circuits of the one or more processors 1700, or loaded from the electronic storage device 1705.

The planogram(s) 1805 is a map of rows and columns of inventory/bin locations. In an aspect of the disclosure, the planogram(s) 1805 are received from the server. In an aspect of the disclosure, the planogram contains identifiers associated with the locations. Since multiple inventory locations, e.g., bins, are associated with a specific platform, a portion of the identifier of locations on the same platform is the same. For example, the identifier of locations/bins for a first platform may have an identifier begin with "A". In an aspect of the disclosure, when the processing circuit 1505 for a platform communicates with the terminal 100, the processing circuit 1505 includes this identifier with the signal. In another aspects, the processing circuit 1505 may include an identifier which is associated with the identifier, e.g., "A^" and the terminal 100 may include a look up table having the association. In another aspect of the disclosure, the identifier is based on an identifier of the weight sensor 55 associated with the platform 45. For example the identifier may be a digital address of the weight sensor 55. This digital address may be sequential and map to a specific platform locations. For example, weight sensors 55 for adjacent platforms may have consecutive digital addresses.

Each location identifier in the planogram may have a unique identifier. This allows for the processor 1700 to determine the location associated with received signals from the processing circuits 1505.

Since the unit 10 is modular, multiple units 10 are able to be connected to the terminal 100. In accordance with this aspect, the terminal 100 may receive multiple phanograms 1805, one for each unit 10.

The display data 1810 contains information for display on one or more screens of the display 1720. The display data 1810 may be received from the server. For example, the terminal 100 may receive schedule codes and operating room identifiers. Additionally, the display data may include a specific indicator to indicate "done", e.g., the adding or removal of a product is complete. The display data 1810 may further include information for an administration screen, including authentication, calibration, etc. In other aspects, the display data 1810 may include warnings such as an indication where products are removed from multiple locations at the same time.

The detection result data 1815 may include the information received from the processing circuits 1505 from one or more platforms 45. Additionally, the detection result data 1815 may include determinations of the locations associated with the information received and the weights (or change in weight) for use in an inventory report and an inventory change report. This information may be temporarily stored and subsequently deleted when an inventory report or an inventory change report is generated and transmitted.

Figure 19:
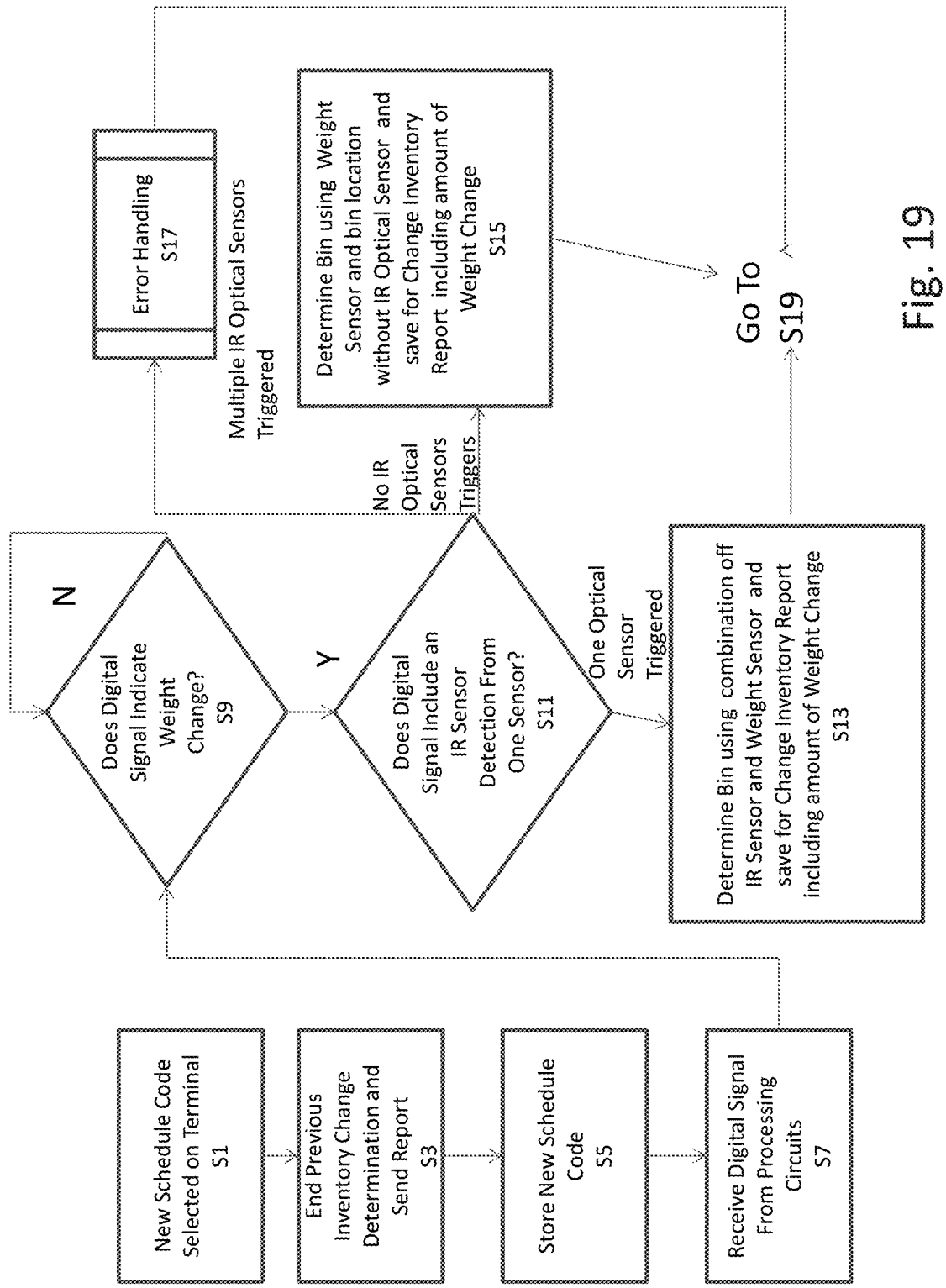
FIGS. 19-23 illustrate flow charts in accordance with aspects of the disclosure.
Figure 20:
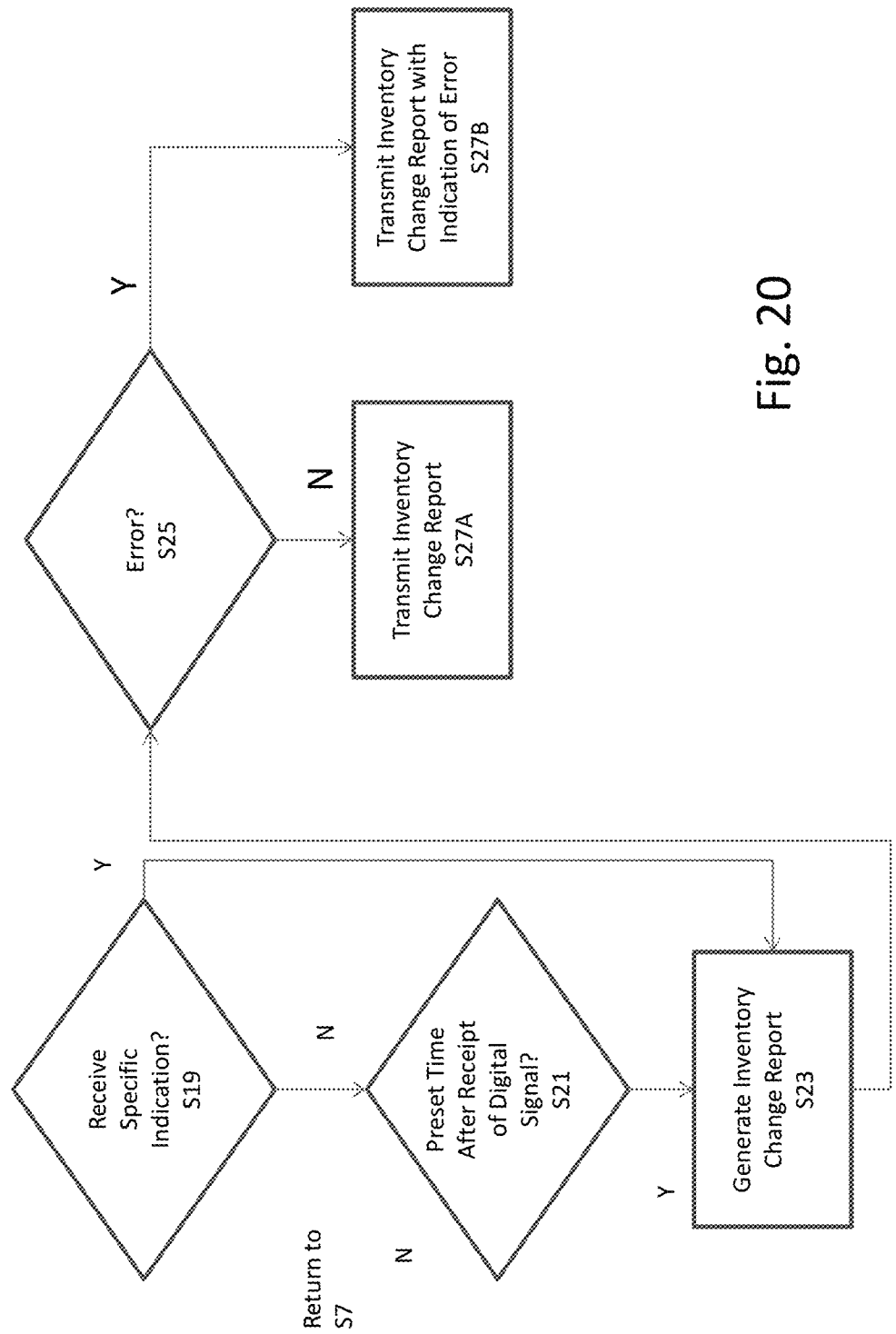

FIGS. 19 and 20 illustrate a flow chart for generating and transmitting an inventory change report in accordance with aspects of the disclosure. The functions described in FIGS. 19 and 20 may be executed by the processor 1700 in the terminal 100. In this aspect of the disclosure, the generation of the inventory change report may be triggered by the receipt of a new schedule code (S1). In an aspect of the disclosure, the terminal 100 may display as a home screen, a screen with schedule codes received from the server. When one of the codes is selected by a person (user), the processor 1705 ends any previous inventory change determinations, completes the inventory change report for the previous event and sends the report to the server (S3). The previous inventory change determination may have been based on another schedule code that was previously selected, restock or replenish. A replenishment process is where new, meaning not previously stored in a bin 30, medical product(s) are placed in bins 30. A restocking process is where medical product(s) which were previously in one of the bins 30 are put back in one of the bins 30.

More specifically, to add one or more medical products to one of the bins 30, through a replenishment process, a user carries one or more new medical products to the unit 10. The user then moves the new medical product, or a container storing one or more new medical products, to a position that a reader (not shown) (such as a bar code reader, a QR code reader, a Radio Frequency Identification (RFID) reader, etc.) can read the identifier of the new medical product or container storing one or more new medical products.

In an aspect of the disclosure, the reader may be a hand-held scanner. For example, the hand-held scanner may be an application in a mobile device. The reader may be configured to communicate directly with the server. In another aspect of the disclosure, the reader may be fixed to any portion of the modular shelving system 1, including any portion of the terminal 100. Also, the reader can be removable from a portion of the modular shelving system 1, such as a wireless barcode scanner. Alternatively, or in conjunction, the user can interact with the terminal 100 and manually enter the number and type of new medical product to be added to a bin 30.

When the reader communicates with the server, the reader may transmit information regarding the type and quantity of the replenished medical product. This information can also include a Stock Keeping Unit (SKU), the expiration of the medical product, the number of products within the package of medical product, etc. In other aspects, the reader may communicate with the terminal 100 and the terminal may relay the information to the server.

Communication with the server and/or terminal 100 can be effected with a communication interface of the reader.

In an aspect of the disclosure, in response to the server receiving the information regarding the replenishing from the reader, the server may request an inventory report (or inventory change report) from the terminal 100 (on-demand report).

Further, to add one or more medical products to one of the bins 30, through a restocking process, a user carries one or more new, but previously removed from the bin 30, medical product(s) from the unit 10. The user then moves the restocked medical product, or a container storing one or more new medical products, to a position that the reader (not shown) can read the identifier of the restocked medical product or container storing one or more restocked medical products.

Similar to above, information regarding the type and quantity of the restocked medical product may be transmitted to the server directly from the reader. In other aspects, the reader may transmit this information to the terminal 100 and the terminal 100 may relay the information to the server. This information can also include a Stock Keeping Unit (SKU), the expiration of the restocked medical product, the number of products of restocked medical product, etc.

In an aspect of the disclosure, in response to the server receiving the information regarding the restocking from the reader, the server may request an inventory report (or inventory change report) from the terminal 100 (on-demand report).

In other aspects of the disclosure, instead of scanning the product for restocking, a user may manually enter the number of units and types of products into a user terminal and place the products back into the appropriate bins 30. For example, the user terminal may be a computer in an operating room or at a nurses station. The user terminal may transmit the number of units and types of products to the server. In an aspect of the disclosure, in response to the server receiving the information regarding the restocking from the user terminal, the server may request an inventory report (or inventory change report) from the terminal 100 (on-demand report).

The server further may reconcile the restocked products by confirming that all of the units and types of products identified by the user on the user terminal matches the number and types of products restocked on the unit based on the inventory report received from the terminal 100 (which includes the location identifier(s) and weights and/or weight changes The generation of the inventory change report and sending will be described in S23, S27A, S28B. At S5, the received schedule code is stored in the electronic storage device 1705. For example, the received schedule code may be stored in the detection result data 1815 as the schedule code may be included in the inventory change report. The terminal 100 waits to receive data from the processing circuits 1505. In an aspect of the disclosure, as described above, the terminal 100 received a signal from a respective processing circuit 1505 when a weight in one of the bins 30 on the associated platform 45 changes more than the preset value (S7). In another aspect, the terminal 100 may continuously receive signals from each processing circuit 1505 regardless of a change in weight at S7. At S9, the processor 1700 determines whether a weight has changed in one (or more) of the platforms. In an aspect of the disclosure, the signal may include the weight or weight change and the processor 1700 reads the weight or weight change. In other aspects of the disclosure, the processor 1700 may determine the weight change by calculating a difference in the weight from two different signals from the same processing circuit (same platform) received at different times. The received signal may include the identifier of the platform. The identifier of the platform and corresponding weight or weight change is stored in the detection result data 1815.

At S11, the processor 1700 determines whether the signal include a detection from one optical sensor 40, e.g., ON (indication thereof). The processing circuit 1505 combines the detections from the weight sensor 55 and the optical sensors 40 into the signal sent to the terminal 100. When the signal includes a detection result, e.g., ON (indication thereof), from only one optical sensor 40 (One Optical Sensor Triggered determination S11), the processor 1700 determines the location of the weight change. The location of the weight change may be determined from a combination of an identifier of the platform 45 (or identifier of the weight sensor 55) and the addressable identifier of the optical sensor 40 which may be included in the signal received from the processing circuit 1505, as the indication. The processing circuit 1505 may include the addressable identifier of the optical sensor 40. The addressable identifier may be based on the in-platform location. The terminal may be programmed with a mapping between the identifier of the platform or weight sensor and locations and a mapping of the addressable identifier of the optical sensor and the specific location, e.g., bin location on a platform. The processor 1700 may use the planogram 1805 to determine the location using the above combination via the mapping. In an aspect of the disclosure, the terminal 100 may have a look-up table with the mapping(s). Once the location is determined, the processor 1700 may log the location identifier from the planogram and the weight or weight change into the detection result data 1815.

When the signal includes an indication that the weight has changed (or the processing 1700 determines the weight has changed) and the processor 1700 determines that the signal received from the processing circuit 1505 does not include an ON detection, e.g., only information of the weight sensor 55, the processor 1700 determines the location based on the identifier of the platform and the following. Optical sensors 40 are associated with N−1 locations on the platform where there are N locations. Therefore, the processor 1700 may determine the location associated with the changed in weight as the location in the platform that is not associated with an optical sensor 40 at S15. Once the location is determined, the processor 1700 may log the location identifier from the planogram (based on the mapping of the identifier of the weight sensor or platform to the locations and the in-platform location associated with no sensor) and the weight or weight change into the detection result data 1815.

When the signal includes an indication that the weight has changed (or the processor 1700 determines the weight has changed) and the processor 1700 determines that the signal received from the processing circuit 1505 include an ON indications from multiple optical sensors 40, e.g., signal contains two or more addresses for optical sensors, the processor 1700 executes an error handling S17. The error handling may include determining the locations in a similar manner as described above and including the weight change for the one or more locations in the detection result data 1815 with a preset flag or indicator. The above process, e.g., S7, S9, S11 and S13 or S15 or S17, is repeated until certain events may occur. The process may be repeated for the same platform or different platforms.

The event includes receiving a specific indication S19 or a preset time after the receipt of a weight change has occurred S21 (time out). In an aspect of the disclosure, the specific indication may be the user pressing a done button on the display 1720. In an aspect of the disclosure, in response to the receipt of a schedule code, the processor 1700 may cause the display 1720 to display a "done" button.

The preset time may be used to account for a user removing a product and subsequently returning the product (either because the wrong product was taken or too many may have been taken). Additionally, the preset time may be used such that if the user forgets is press "done" after completing the removal of products, such as medical products for a single medical procedure, the change report may be sent to the server. In an aspect of the disclosure, the preset time may be 10 minutes after a receipt of a weight change on any of the platforms 45 (processing circuits 1505). In this aspect of the disclosure, the processor 1700 may also record the time of receipt of the signal from each processing circuit 1505.

At S19, the processor 1700 determines whether the user pressed the "done" button on the screen (area associated with the same). When the processor 1700 determines that the button was pressed ("Y" at S19), the processor 1700 generates the change inventory report for the schedule code at S23. When the processor 1700 determines that the button on the screen has not been pressed ("N" at S19), the processor 1700 determines whether the preset time after receive of any weight change has expired. For example, in an aspect of the disclosure, the processor 1700 may set a timer when a signal indicating a weight change is received. The timer may be set to the preset time. When a new signal indicating a weight change is received, the timer is reset to the preset time (an example of "N" at S21). When the timer expired, the processor 1700 may determine that the preset time is reached, e.g., "Y" at S21, and generates the inventory change report.

In other aspects of the disclosure, instead of a timer, the processor 1700 may use time stamps associated with the reception of the signal from a processing circuit 1505 and a current time. When the difference equals the preset time, the processor 1700 may determine that the preset time is reached, e.g., "Y" at S21.

At S23, the processor 1700 generates the inventory change report. The processor 1700 retrieves the detection result data 1815 from the electronic storage device and aggregates the data. For each location, any weight change is aggregated to obtain a final weight change. For example, if the same location has five signals indicating a weight change (five weight changes), the processor 1700 combines the weight changes to get the final weight change. If the weight changes are +3 g, +3 g, −3 g, +3 g and +3 g, the final weight change is +9 g. The inventory change report may contain the location identifiers (platform and location on the platform) and final weight change for each location having a change.

In other aspects of the disclosure, instead of aggregating the data, the processor 1700 generates the inventory change report to include each line item of information, e.g., each weight change. For example, the inventory change report may include the location identifier, the weight change and a time stamp of the weight change (or time of the receipt of the signal) for each change.

Prior to sending the inventory change report, the processor 1700 may determine whether error handling is required at S25. For example, as described above when multiple optical sensors 40 detect an ON (at the same time), error handling S17 occurs and a flag is set. If the error flag is set for a particular location, the inventory change report is sent to the server by the terminal 100 with an indication of the error at S27B otherwise, the inventory change report is sent to the server without an indication at S27A. For example, the indication may indicate which location(s) were affected. This is to notify the server that the weight change for the locations may not be correct and may not be able to be used to determine the number of products removed or added.

The processor 1700 sends the inventory change report (without or with indication) to the server using the second communication interface 1715, e.g., wireless communication interface.

The generation of an inventory change report may also be triggered by the receipt of a signal indicating a weight change from one or more of the processing circuits 1505.

Figure 21:
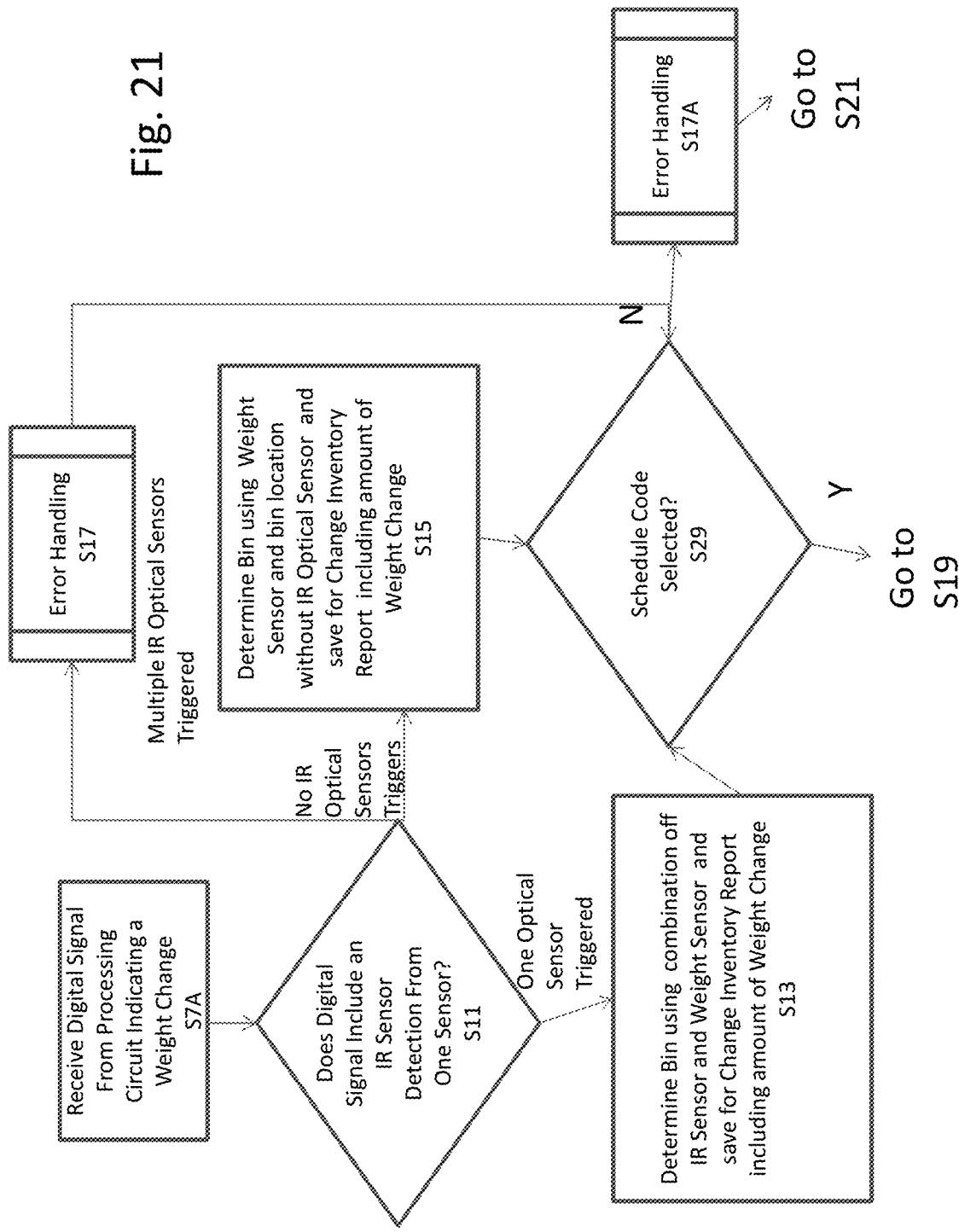

FIG. 21 illustrates a flow chart for functions of the terminal 100 when the process is triggered by the receipt of a signal indicating a weight change (the process continues to FIG. 20 after either S29 or S17A. with adding a flag indicating that the schedule code was not received).

As described above, the terminal 100 may continuously receive signals from the processing circuits 1505. Here, at S7A the signal may indicate a change in weight on a platform. Alternatively, as described above, the processor 1700 may determine whether the weight has changed based on the receipt of two successively signals from the same processing circuit. After receipt thereof, S11 is performed and depending on the determination either S13, S15 or S17 is performed. In an aspect of the disclosure, the processor 1700 obtains the location identifier of the platform (or location identifier of the weight sensor 55) and weight from the signal and if included the address of the optical sensor.

The processor 1700 also determines whether the user has selected a schedule code on the display 1720 at S29. If the processor determines that a schedule code has not been selected, the processor 1700 proceeds to S17A, error handling. Error handling at S17A still includes recording the location(s) and weight into the detection result data 1815, however, it may also include setting a flag indicating that no schedule code is received. This is to alert the server that inventory may have changed, but that no schedule code was received.

Prior to the inventory change report being sent to the server, and the determination of error at S25 is made by the processor 1700, the determination may also include determining whether the flag indicating that no schedule code is set.

After an inventory change report is sent, the data in the detection result data 1815 may be deleted. In other aspects, the data may be held for a predetermined period of time such as one day.

Figure 22:
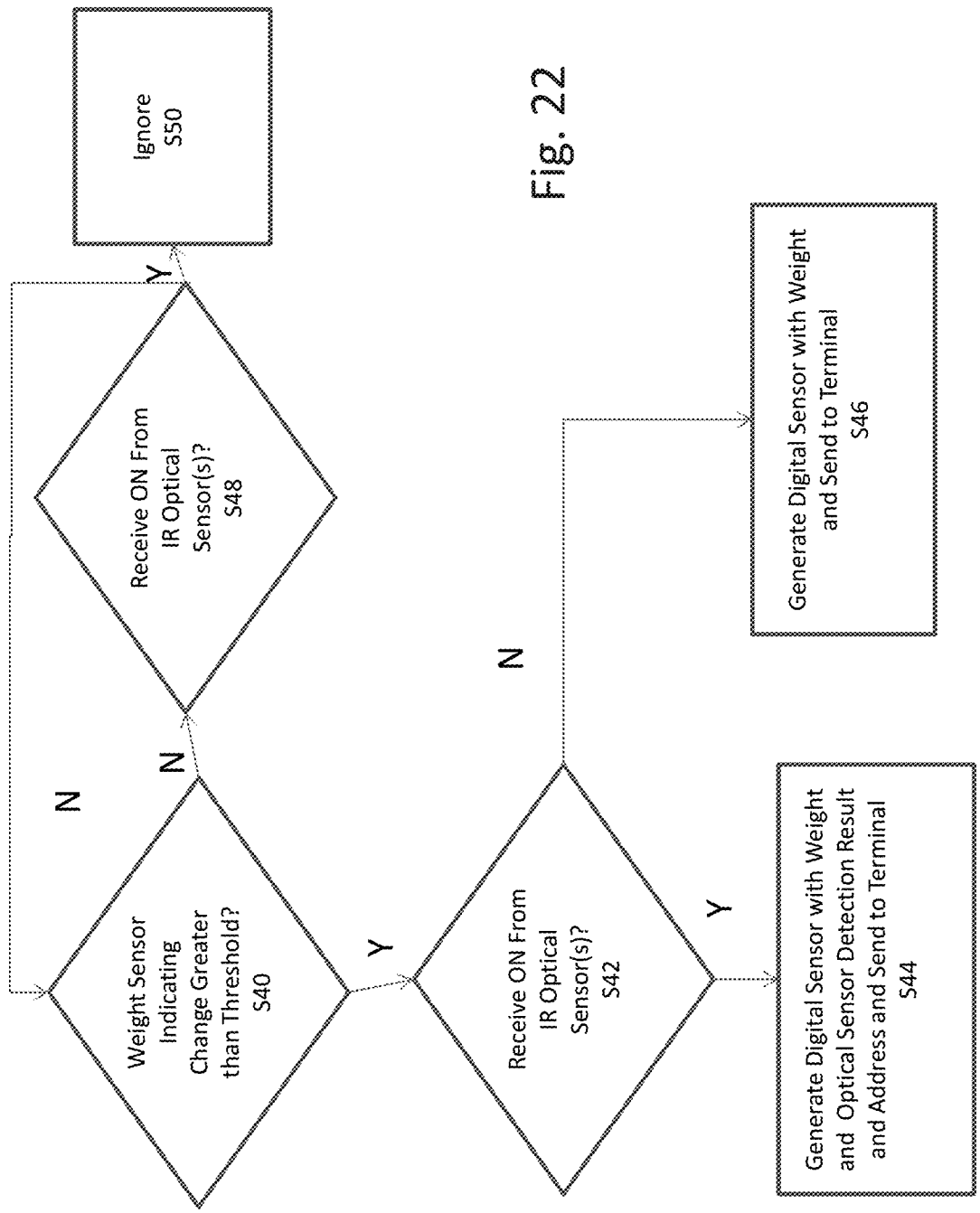

FIG. 22 illustrates a flow chart for the processing circuit 1505 in accordance with aspects of the disclosure. At S40, the processing circuit 1505 determines whether the weight sensor 55 indicates a weight change greater than the preset value. As described above, the weight sensor may alternatively make an initial determination of the change of weight and compare with the preset value (threshold) prior to sending a signal to the processing circuit 1505, e.g., signal only sent if greater. Therefore, the determination may be that a signal is received from the weight sensor 55. Also as described above, the processor in the processing circuit 1505 may determine the weight or change in weight based on a measured voltage. S40 may also include this determination and subsequent comparison with the preset value. When there is a determination of a weight change (greater than the threshold), the processor in the processing circuit 1505 determines whether it receive an ON signal from an optical sensor(s) 40 at S42. When an ON signal is received from one or more optical sensors 40 ("Y" at S42), the processor in the processing circuit 1505 generates a signal to transmit to the terminal at S44. The signal may include an identifier of the platform (or identifier of the weight sensor 55), the determined weight or weight change and the address(es) of the optical detector(s). The processor transmits this signal via the RS485 communication bus 1600 to the terminal 100.

When no signal is received from an optical sensor 40 ("N" at S42), the processor generates a signal to transmit to the terminal at S46. The signal may include an identifier of the platform (or the identifier of the weight sensor 55) and the determined weight or weight change.

When the processor in the processing circuit 1505 determines that there is no weight change or the weight change is less than the preset value ("N"), the processor in the processing circuit further determines whether a signal is received from an optical sensor 40 at S48, e.g., On signal. If the signal is received ("Y" at S48), the signal may be ignored at S50. If a signal is not received from any optical sensor 40 ("N" at S48), the processor in the processing circuit 1505 waits for signals from either the weight sensor 55 or optical sensors 40.

Figure 23:
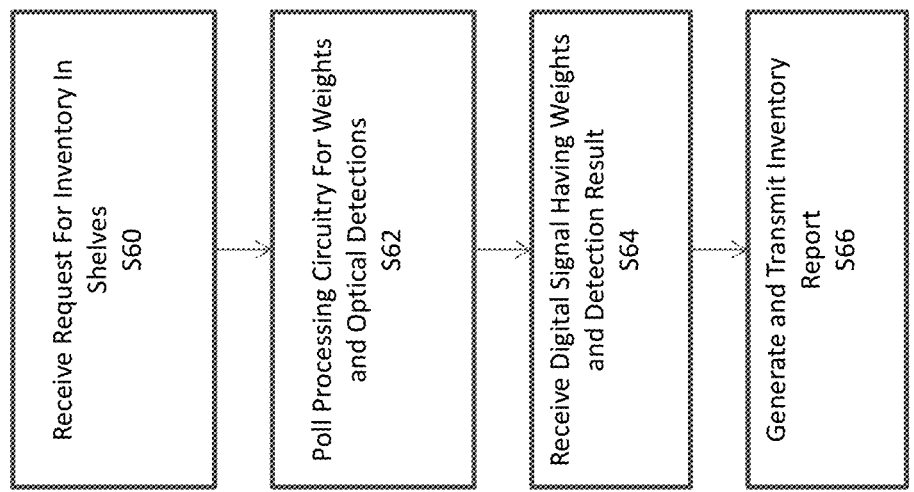

The modular shelving unit 10 may also receive to an on-demand request from the server. FIG. 23 illustrates a flow chart for responding to the on-demand request from the server.

At S60, the processor 1700 receives a request from the server for an inventory report. In response to receipt of the request, the processor 1700 polls each of the processing circuits 1505 for detection results. The polling may be sequentially. For example, the polling may be in the order of location based on the planogram 1805. The polling request is transmitted to the processing circuits 1505 via the communication bus 1600. When the request is received by the processor in the processing circuits 1505, the processor may determine the current weight on the platform. For example, the processor may receive a measurement of the voltage across the strain gauge and determine the weight therefrom as described above. In other aspects of the disclosure, the processor in the processing circuits 1505 may request the weight sensor 55 to send a signal indicating the voltage or the current weight. For example, as described above, the weight sensor 55 may comprise electric circuitry to determine the voltage and the weight and output the weight or weight change when the weight or weight change exceeds the preset value. In this aspect, the weight sensor 55 may transmit the signal responsive to the request.

The processor in the processing circuit 1505n also determines whether any signal has been received from the optical sensors 40. If no signal is received from the optical sensor, the processor in the processing circuit 1505 generates a signal including the identifier of the platform and the current weight and transmits the signal to the terminal 100 via the communication bus. If an ON signal is received from one or more optical sensors 40, the processor in the processing circuit 1505 generates a signal including the identifier of the platform, the current weight and address(es) of the optical sensors and transmits the signal to the terminal 100 via the communication bus.

At S64, the processor 1700 receives the signal from the processor in the processing circuit 1505 (for one platform), identifies the location as described above and records the weight and location(s) into the detection result data 1815. This is repeated for each platform 45.

Once the information is obtained for all platforms 45 (from each processing circuit 1505), the processor 1700 generate the inventory report. The inventory report may include the identifier of each platform (or weight sensor) from the planogram and the current weight, respectively retrieved from the detection result data. The inventory report may also include the location of any optical detection. The processor 1700 transmits the inventory report to the server via the second communication interface 1715.

In other aspects of the disclosure, instead of the processing circuit 1505 for each platform 45 determining the weight or weight change (or the weight sensor), the processing circuit 1505 may act as a relay in relay the measurement data from the weight sensor (and the optical sensor) to the terminal 100 and the terminal may determine the weight or weight change from the measurement data.

In an aspect of the disclosure, the server may include both the planogram for each unit 10 and an inventory map. The inventory map includes the identifier of a product in each product location in the planogram. In an aspect of the disclosure, the inventory map may also include the weight of one unit of the product. Therefore, the server in response to the receipt of the weight and location (or weight change) and location may determine the number of units in the inventory location (in a bin 30), number added or number removed. The number of units may be determined by dividing the weight received by the weight per unit. The number of units added similarly may be determined by dividing the weight change by the weight per unit.

In an aspect of the disclosure, the inventory change report may include a time stamp of the changes such that when the same platform includes a weight change, the time stamp may be used in combination with the location and weights to determine the number of units added or subtracted.

In an aspect of the disclosure, the unit 10 may be located outside of an operating room but within a core of operation rooms. The unit 10 may also be located in the operating room.

In an aspect of the disclosure, the weight sensors 55 and optical sensors 40 may be calibrated when the unit 10 is installed, such as in a hospital. For example, medical products have a known weight may be placed in the bins 30 and the voltage measured and weight determined to confirm that the weight sensor is correct. In other aspects of the disclosure, the calibration may use a known weight, such as 2.5 Kg for the testing of each load sensor. Further, measurements may be made without a weight but with the bins 30 such that a reported weight or weight change to the terminal 100 is the weight of the products (weight change) without the weight of the bins. In an aspect of the disclosure, the processing circuit assumes all of the bins 30 (for its bin locations) are placed on the platform when determining the weight or weight change. For example, when are three bin locations on a platform 45, a processing circuit 1505 may subtract the weight (of the three empty bins) from the weight or the weight change.

As used herein, the term "processor" may include a single core processor, a multi-core processor, multiple processors located in a single device, or multiple processors in wired or wireless communication with each other and distributed over a network of devices, the Internet, or the cloud. Accordingly, as used herein, functions, features or instructions performed or configured to be performed by a "processor", may include the performance of the functions, features or instructions by a single core processor, may include performance of the functions, features or instructions collectively or collaboratively by multiple cores of a multi-core processor, or may include performance of the functions, features or instructions collectively or collaboratively by multiple processors, where each processor or core is not required to perform every function, feature or instruction individually.

The phrase "communication interface" includes electronic circuitry, configured for one or more specific standards, that enables one device to telecommunicate transmit and receive) with another device.

The various aspects disclosed herein can be implemented in various forms of hardware, software, firmware, and/or special purpose processors. For example, in an aspect of the disclosure, at least one non-transitory computer readable storage medium has instructions encoded thereon that, when executed by one or more processors, cause one or more of the aspects disclosed herein to be implemented. The instructions can be encoded using a suitable programming language, such as C, C++, object oriented C, Java, JavaScript, Visual Basic .NET, Beginner's All-Purpose Symbolic Instruction Code (BASIC), or alternatively, using custom or proprietary instruction sets. The instructions can be provided in the form of one or more computer software applications and/or applets that are tangibly embodied on an electronic storage device, and that can be executed by a computer having any suitable architecture. The computer software applications disclosed herein may include any number of different modules, sub-modules, or other components of distinct functionality, and can provide information to, or receive information from, still other components.

Numerous specific details have been set forth herein to provide a thorough understanding of the disclosure. It will be understood by an ordinarily-skilled artisan, however, that the aspects of the disclosure may be practiced without these specific details. In other instances, well known operations, components and circuits have not been described in detail so as not to obscure the disclosure. It can be appreciated that the specific structural and functional details disclosed herein may be representative and do not necessarily limit the scope of the aspects of the disclosure. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, and aspects have been described herein. The feature and aspects are susceptible to combination with one another as well as to variation and modification, as will be understood by those having skill in the art. The present disclosure should, therefore, be considered to encompass such combinations, variations, and modifications. It is intended that the scope of the present disclosure not be limited by this detailed description, but rather by the claims appended hereto. Future filed applications claiming priority to this application may claim the disclosed subject matter in a different manner, and may generally include any set of one or more elements as variously disclosed or otherwise demonstrated herein.

While the present disclosure has been particularly shown and described with respect to preferred aspects thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A modular shelving unit comprising:
a shelf which is placeable on a rack, the shelf comprising a platform disposed on a weight sensor, wherein the platform is configured to support X holders, wherein X is a first number and each of the X holders is configured to store products, wherein each shelf further comprises:
Y optical sensors disposed below Y holders when the Y holders are disposed on the platform, wherein Y is a second number that is one less than X, the Y optical sensors being in proximity of the Y holders, respectively, wherein each holder includes an opening which is aligned with one of the Y optical sensors when the holder is disposed on the shelf, and a processing circuit coupled to the Y optical sensors and the weight sensor, the processing circuit configured to:
(i) receive either a first output from the weight sensor and a second output from one or more of the Y optical sensors or the first output from the weight sensor without the second output;
(ii) convert the respective outputs into a digital signal that comprises:
(a) an identifier of the weight sensor and an identifier of the one or more optical sensors when both the first output and the second output are received by the processing circuit; or
(b) when the second output is not received, an identifier of the weight sensor and an indication of a weight or weight change associated with the first output from the weight sensor; and
(iii) transmit the digital signal to a terminal.

2. The modular shelving unit of claim 1, wherein the shelf comprises:
a plurality of platforms, each of which includes a corresponding weight sensor, X holders, Y optical sensors below Y holders when the Y holders are disposed on the platform,
wherein each holder includes an opening, wherein when a holder is on the shelf, the opening is capable of being aligned with an optical sensor, the shelf further having a plurality of processing circuits, each of which corresponds to one of the plurality of platforms.

3. The modular shelving unit of claim 2, further comprising a shelving assembly comprising at least two of the shelves, the shelving assembly further comprising a wall connecting the shelves, wherein the plurality of processing circuits in the shelves are connected to each other via wires mounted to or in the wall.

4. The modular shelving unit of any of claim 1, 2 or 3, further comprising the terminal connected to the processing circuit or processing circuits.

5. The modular shelving unit of claim 4, wherein information contained in the digital signal is usable to determine a number of products within each respective holder, number of products removed from respective holders or number of products added to respective holders.

6. The modular shelving unit of claim 4, wherein the at least two shelf assemblies are connected to each other and with the terminal.

7. The modular shelving unit of any of claims 1-6, wherein X is 3 and Y is 2.

8. The modular shelving unit of any of claims 1-7, wherein the modular shelving unit is configured to be connected to another modular shelving unit and to the terminal.

9. The modular shelving unit of claim 4 or 5, wherein the terminal comprises a touch panel, and wherein the touch panel is configured to display at least one of a scheduled procedure identifier or an operating room identifier.

10. The modular shelving unit of claim 9, wherein after a receipt of at least the scheduled procedure identifier or the operating room identifier, the terminal is configured to transmit an inventory change report to a server with the received at least one of the scheduled procedure identifier or the operating room identifier and information contained in the digital signal received from the processing circuit or processing circuits.

11. The modular shelving unit of claim 10, wherein the terminal is configured to transmit the inventory change report only after a receipt of a preset selection on the touch panel or after a preset time from the receipt of the digital signal from the processing circuit or processing circuits.

12. The modular shelving unit of claim 9, wherein the terminal is configured to receive a request for an inventory report from the server, wherein in response to the request, the terminal is configured to poll the processing circuit or processing circuits for detection results.

13. The modular shelving unit of claim 12, wherein the terminal is configured to generate the inventory report based on the information received from the processing circuit or processing circuits.

14. The modular shelving unit of claim 9, wherein the terminal is configured to periodically poll the processing circuit or processing circuits for detection results.

15. The modular shelving unit of claim 9, wherein the terminal is configured to transmit the inventory change report to the server with an error indicator when the digital signal indicates a decrease in weight without receiving the scheduled procedure identifier or the operating room identifier.

16. The modular shelving unit of claim 9, wherein the terminal is configured to receive the scheduled procedure identifier or the operating room identifier from the server.

17. The modular shelving unit of claim 9, wherein in response to the receipt of the digital signal containing the identifier only of the weight sensor, the terminal device associates the indication of weight or weight change with a bin location other than a bin location associated with an optical sensor.

18. The modular shelving unit of claim 1, wherein the indication of weight or weight change is selected from a group consisting of a weight or weight change, a measured voltage or change in a measured voltage or a determined resistance or a determined change in resistance.

19. The modular shelving unit of claim 18, wherein the terminal determines the weight change based on two consecutive digital signals received from a respective processing circuit.

20. The modular shelving unit of claim 19, wherein the identifier of the weight sensor and/or identifiers of the one or more optical sensors is used to determine a bin location of the weight change.

* * * * *